United States Patent
Vanberlo et al.

(10) Patent No.: US 12,373,926 B1
(45) Date of Patent: Jul. 29, 2025

(54) COMPUTING SYSTEMS AND METHODS FOR MASKING ULTRASOUND IMAGES

(71) Applicant: Deep Breathe Inc., London (CA)

(72) Inventors: Blake Vanberlo, Lucan (CA); Delaney Smith, Port Perry (CA); Jordan Ho, Toronto (CA); Marwan Rahman, Mississauga (CA); Benjamin Huggard, Bedford (CA); Joshua Kurien, Mississauga (CA)

(73) Assignee: Deep Breathe Inc., London (CA)

( * ) Notice: Subject to any disclaimer, the term of this patent is extended or adjusted under 35 U.S.C. 154(b) by 0 days.

(21) Appl. No.: 18/935,011

(22) Filed: Nov. 1, 2024

Related U.S. Application Data

(60) Provisional application No. 63/557,167, filed on Feb. 23, 2024.

(51) Int. Cl.
*G06T 7/70* (2017.01)
*A61B 8/00* (2006.01)
(Continued)

(52) U.S. Cl.
CPC .............. *G06T 5/70* (2024.01); *A61B 8/5207* (2013.01); *G06T 5/60* (2024.01); *G06T 7/13* (2017.01);
(Continued)

(58) Field of Classification Search
CPC .... G06T 5/70; G06T 5/60; G06T 7/13; G06T 7/50; G06T 7/73; G06T 7/90;
(Continued)

(56) References Cited

U.S. PATENT DOCUMENTS 10,991,097 B2 * 4/2021 Yip ........................ G06V 20/69
12,254,677 B2 * 3/2025 Toporek ................ G06T 7/0012
(Continued)

FOREIGN PATENT DOCUMENTS

WO    WO-2023070946 A1 *  5/2023

OTHER PUBLICATIONS

Moi Hoon Yap et al. Automated Breast Ultrasound Lesions Detection Using Convolutional Neural Networks. IEEE Journal of Biomedical and Health Informatics, vol. 22, No. 4, Jul. 2018; first published Aug. 8, 2017, pp. 1218-1226.
(Continued)

*Primary Examiner* — Jose L Couso
(74) *Attorney, Agent, or Firm* — Marks & Clerk; Jennifer Davy

(57) ABSTRACT

Systems and methods for automatically masking an ultrasound image are provided. A computing system is configured to: automatically compute within the ultrasound image a set of keypoints that define an estimated shape of an ultrasound beam image within the ultrasound image; automatically select, using the set of keypoints, a beam geometry from amongst a set of known beam geometries; automatically modify the set of keypoints based on the beam geometry to generate a modified set of keypoints that defines a modified shape of the ultrasound beam image; automatically compute a binary mask configured to mask pixels around the modified shape of the ultrasound beam image using at least the modified set of keypoints and the beam geometry; and automatically compute and output a masked ultrasound image using at least the binary mask.

29 Claims, 19 Drawing Sheets

(51) Int. Cl.

| | |
|---|---|
| *G06T 5/60* | (2024.01) |
| *G06T 5/70* | (2024.01) |
| *G06T 7/13* | (2017.01) |
| *G06T 7/50* | (2017.01) |
| *G06T 7/73* | (2017.01) |
| *G06T 7/90* | (2017.01) |
| *G06V 10/82* | (2022.01) |
| *G06V 30/19* | (2022.01) |

(52) U.S. Cl.
CPC ............... *G06T 7/50* (2017.01); *G06T 7/73* (2017.01); *G06T 7/90* (2017.01); *G06V 10/82* (2022.01); *G06V 30/19* (2022.01); *G06T 2207/10016* (2013.01); *G06T 2207/10024* (2013.01); *G06T 2207/10132* (2013.01); *G06T 2207/20084* (2013.01); *G06T 2207/30004* (2013.01)

(58) Field of Classification Search
CPC . G06T 2207/10016; G06T 2207/10024; G06T 2207/10132; G06T 2207/20084; G06T 2207/30004; G06T 7/0012; G06T 2207/10136; G06T 2207/30048; G06T 17/00; G06T 2207/10116; G06T 2207/10004; G06T 2207/30101; G06T 2210/41; G06T 7/11; G06T 7/60; G06T 7/62; G06T 2207/30044; G06T 2207/30012; G06T 2207/30061; G06T 2207/30068; G06T 15/205; G06T 2200/24; G06T 2207/20036; G06T 2210/12; G06T 3/4046; G06T 9/002; G06T 2207/20076; G06T 2207/20081; A61B 8/5207; A61B 8/5223; A61B 8/0866; A61B 8/463; A61B 8/0883; A61B 8/065; A61B 8/468; A61B 8/469; A61B 8/488; G06V 10/82; G06V 30/19; G06V 10/46; G06V 10/454; G06V 10/54; G06V 10/774; G06V 20/41; G06V 30/18057; G06V 20/698; G06V 30/19173; G16H 30/20; G16H 30/40; G16H 50/20; G16H 50/30; G06N 3/02; G06N 3/08–088; G06N 3/0445; G06N 3/0454; G06N 3/4046; G06N 7/00; G06N 7/01; G06N 20/00; G06K 7/1482; G06F 18/214; G06F 18/22; G06F 18/241; G06F 18/24; G06F 18/2411; G06F 18/2415; Y10S 128/925

See application file for complete search history.

(56) References Cited

U.S. PATENT DOCUMENTS

| | | | | |
|---|---|---|---|---|
| 12,256,075 | B2* | 3/2025 | Besenbruch | G06N 3/084 |
| 2011/0317897 | A1* | 12/2011 | Narasimhamurthy | G06T 7/215 |
| | | | | 382/128 |
| 2013/0223704 | A1* | 8/2013 | Lay | G06T 7/11 |
| | | | | 382/128 |
| 2015/0023577 | A1* | 1/2015 | Li | G06T 7/62 |
| | | | | 382/131 |
| 2015/0087982 | A1* | 3/2015 | Mullick | G16H 50/30 |
| | | | | 600/443 |
| 2016/0275678 | A1* | 9/2016 | Onal | G06V 10/50 |
| 2020/0093464 | A1* | 3/2020 | Martins | A61B 8/12 |
| 2020/0113544 | A1* | 4/2020 | Huepf | G06T 7/60 |
| 2021/0056691 | A1* | 2/2021 | Gernand | G06N 3/08 |
| 2021/0113174 | A1* | 4/2021 | Xu | G06T 7/33 |
| 2022/0222825 | A1* | 7/2022 | Yaacobi | G06T 3/4007 |
| 2023/0099970 | A1* | 3/2023 | Luo | G01S 7/52063 |
| | | | | 600/443 |
| 2023/0346337 | A1 | 11/2023 | Duffy et al. | |
| 2024/0423583 | A1* | 12/2024 | Gardella | A61B 8/0883 |

OTHER PUBLICATIONS

Madani et al. Deep echocardiography: data-efficient supervised and semi-supervised deep learning towards automated diagnosis of cardiac disease. NPJ Digital Medicine (2018) 59; published online Oct. 18, 2018, pp. 1-11.

Chi-Jim Chen et al. Prediction of chronic kidney disease stages by renal ultrasound imaging. Enterprise Information Systems, 2020, vol. 14, No. 2, published online Mar. 26, 2019, pp. 178-195.

Arntfield et al. Automation of Lung Ultrasound Interpretation via Deep Learning for the Classification of Normal versus Abnormal Lung Parenchyma: A Multicenter Study. Diagnostics 2021, 11, 2049; published Nov. 4, 2021, 17 pages.

Newhauser et al. Anonymization of DICOM electronic medical records for radiation therapy. Computers in Biology and Medicine, 53 (2014); published Jul. 26, 2014, pp. 134-140.

Orekondy et al. Connecting Pixels to Privacy and Utility: Automatic Redaction of Private Information in Images. 2018 IEEE/CVF Conference on Computer Vision and Pattern Recognition, published Jun. 2018, pp. 8466-8475.

Shahid et al. A Two-Stage De-Identification Process for Privacy-Preserving Medical Image Analysis. Healthcare 2022, 10, 755; published Apr. 19, 2022, 25 pages.

Clunie and Gebow. Block selective redaction for minimizing loss during de-identification of burned in text in irreversibly compressed JPEG medical images. Journal of Medical Imaging 2(1), 016501 (Jan.-Mar. 2015); published online Mar. 25, 2015, 6 pages.

Ebadi et al. COVIDx-US—An Open-Access Benchmark Dataset of Ultrasound Imaging Data for AI-Driven COVID-19 Analytics. arXiv:2103.10003, first published Mar. 18, 2021, 14 pages.

Dadoun et al. Combining Bayesian and Deep Learning Methods for the Delineation of the Fan in Ultrasound Images. 2021 IEEE 18th International Symposium on Biomedical Imaging (ISBI), Nice, France; published Apr. 2021, pp. 743-747.

Tan and Le. EfficientNet: Rethinking Model Scaling for Convolutional Neural Networks. Proceedings of the 36th International Conference on Machine Learning, Long Beach, California, PMLR 97, 2019; published Jun. 2019, 10 pages.

Huber. Robust Estimation of a Location Parameter. The Annals of Mathematical Statistics, vol. 35(1), published Mar. 1964, pp. 73-101.

Extended European Search Report issued Apr. 7, 2025 in related EP Patent Application No. 24211262.1 (8 pages).

Pare et al. Transfer Learning for Automated COVID-19 B-Line Classification in Lung Ultrasound. 2022 44th Annual International Conference of the IEEE Engineering in Medicine & Biology Society (EMBC), published Jul. 11, 2022, pp. 1675-1681.

Tanno et al. AutoDVT: Joint Real-Time Classification for Vein Compressibility Analysis in Deep Vein Thrombosis Ultrasound Diagnostics. Medical Image Computing and Computer Assisted Intervention—MICCAI 2018; [Lecture Notes in Computer Science], Springer International Publishing, CHAM, published Sep. 26, 2018, pp. 905-912.

Prieto et al. An automated framework for image classification and segmentation of fetal ultrasound images for gestational age estimation. Author Manuscript. Medical Imaging 2021: Image Processing, published Feb. 15, 2021, 17 pages.

Tsui and Chan. Automatic Selective Removal of Embedded Patient Information from Image Content of DICOM Files. American Journal of Roentgenology, vol. 198(4), published Apr. 1, 2012, pp. 769-772.

\* cited by examiner

COMPUTING SYSTEMS AND METHODS FOR MASKING ULTRASOUND IMAGES

CROSS-REFERENCE TO RELATED APPLICATION

This present application claims priority to U.S. Provisional Patent Application No. 63/557,167, filed on Feb. 23, 2024, and titled "COMPUTING SYSTEMS AND METHODS FOR MASKING ULTRASOUND IMAGES", the entire contents of which are hereby incorporated by reference.

TECHNICAL FIELD

The disclosed exemplary embodiments relate to computer-implemented systems and methods for automatically masking ultrasound images.

BACKGROUND

Ultrasound examinations are increasingly the subject of studies seeking to apply deep learning to the interpretation of medical images. Ultrasound images are constructed from the transduced amplitudes of sound waves that are reflected by tissues back at the ultrasound probe. The shape of the ultrasound beam is dependent on several attributes, and it may not be rectangular. The ultrasound beam location and shape vary greatly by manufacturer, machine, probe, and other imaging settings. On a standard ultrasound image, the beam is situated within a larger rectangular array of black pixels, which is typically populated with extraneous graphical entities. Unlike the effortlessly removable graphical entities provided through picture archiving and communication systems (PACS), some artifacts may be directly imprinted into the image itself. Such artifacts that surround or overlay the beam are typically referred to as "burnt-in", as they cannot be readily expunged due to the absence of positional and/or morphological metadata in the image file. On ultrasound images, burnt-in artifacts may include probe markers, textual clinician annotations, ultrasound settings, personal health information (PHI), vendor logos, guidance markers, and other extraneous graphics. Examples of these artifacts are provided in FIGS. 1A, 1B, 1C, 1D. FIG. 1A shows an example rectangular image 102 that includes a phased array ultrasound beam image 103 and various artifacts 2. The example rectangular image 102 is from a first example manufacturer of ultrasound imaging devices. FIG. 1B shows an example rectangular image 104 that includes a curved linear array ultrasound beam image 105 and various artifacts 2. The example rectangular image 104 is from a second example manufacturer of ultrasound imaging devices. FIG. 1C shows an example rectangular image 106 that includes a linear array ultrasound beam image 107 and various artifacts 2. The example rectangular image 106 is from the first example manufacturer of ultrasound imaging devices. FIG. 1D shows an example rectangular image 108 that includes a phased array ultrasound beam image 109 and various artifacts 2. The example rectangular image 108 is from a third example manufacturer of ultrasound imaging devices. It will be appreciated that the ultrasound images and the artifacts vary between different manufacturers and different ultrasound imaging devices. More generally, a frame from an ultrasound video, or an ultrasound image, or both, include a set of pixels that convey the ultrasonic information received by an ultrasonic transducer. The rectangular images 102, 104, 106, 108 are also herein called ultrasound images, and each of the ultrasound images 102, 104, 106, 108 respectively include the ultrasound beam images 103, 105, 107, 109.

In some cases, ultrasound images from the ultrasound imaging devices that have been unedited or have not been visually modified are considered raw ultrasound images. The inclusion of raw ultrasound images in datasets for training deep learning models is problematic for two core reasons. First, the presence of device vendor logos and clinical annotations are examples of features in the input that may be exploited by the optimization process for deep learning models. For instance, the co-occurrence of institutional vendor contracts and geographical prevalence for specific conditions may produce spurious correlations that may not generalize to other healthcare institutions. In some cases, for segmentation problems, edges of the ultrasound beam are to be clearly demarcated to facilitate efficient labelling by clinicians. In some cases, without predefined guides depicting the bounds of the beam, different labelers may apply different contours, particularly in darker regions of the beam. In some cases, the second reason for their removal is to preserve patients' right to privacy, since identifying information may be present as burnt-in text. It is incumbent on model developers to remove any protected health information (PHI) that is present on ultrasound images comprising a training set. Therefore, a pivotal component of the cleaning process for ultrasound datasets is the removal of all textual and graphical artifacts that are positioned outside the perimeter of the ultrasound beam. Previous work on this front has used a multitude of techniques to insert redacting blocks over top of detected text. Although effective for privacy purposes, these methods create other graphical artifacts in predefined areas that can still be exploited during model training, resulting in untrustworthy models.

In general, the position and form of ultrasound beams do not vary for ultrasound beams of the same machine, probe, preset, and depth. It is herein recognized that datasets acquired under consistent conditions may be cleaned by applying a known mask to the ultrasound images to isolate the beam. However, a means for efficiently removing extraneous artifacts and information from the ultrasound beam (hereafter referred to as "masking") is useful for deep learning development involving heterogenous datasets composed of samples from multiple devices, vendors, and probe types. Without such a tool, developers are obliged to manually delineate the shape of the beam or to handcraft situation-specific procedures (e.g., the public COVIDxUS dataset). The public COVIDxUS dataset is explained in further detail in the publication Ebadi A. et al, "COVIDx-US: An Open-Access Benchmark Dataset of Ultrasound Imaging Data for AI-Driven COVID-19 Analytics", Front Biosci (Landmark Ed), 2022 Jun. 24; 27(7): 198.

In some cases, one of the ways to remove all the artifacts and provide adequate demarcation of the beam for model training is to delineate the borders of the beam itself. Existing methods include an initial dataset of masked ultrasound images that was generated using parametric curves, then used to train a U-Net for automatic masking. This method was effective when the beam was isolated within the image and fully visible but would generate inaccurate masks if the periphery of the beam was dark or had artifacts directly adjacent to it. In some cases, this method is not applicable to images from unseen vendors or probe types, as it only exploits the geometrical properties of the beam for a particular set of vendors. For example, this method does not generalize to linear probe types. Semantic segmentation approaches that attempt to predict which pixels belong to the beam are also insufficient because they do not always predict the correct beam shape when peripheral regions are dark.

SUMMARY

The following summary is intended to introduce the reader to various aspects of the detailed description, but not to define or delimit any invention.

In at least one broad aspect, there is provided a system for masking an ultrasound image, comprising: a memory storing instructions; and a processor coupled to the memory. The processor is configured to execute the instructions to: automatically compute within the ultrasound image a set of keypoints that define an estimated shape of an ultrasound beam image within the ultrasound image; automatically select, using the set of keypoints, a beam geometry from amongst a set of known beam geometries; automatically modify the set of keypoints based on the beam geometry to generate a modified set of keypoints that defines a modified shape of the ultrasound beam image; automatically compute a binary mask configured to mask pixels around the modified shape of the ultrasound beam image, using at least the modified set of keypoints and the beam geometry; and automatically compute and output a masked ultrasound image using at least the binary mask.

In some cases, the set of keypoints comprises points p1, p2, p3, and p4, wherein p1 refers to a coordinate $(x_1,y_1)$ at a top left corner of the estimated shape of the ultrasound beam; p2 refers to a coordinate $(x_2,y_2)$ at a top right corner of the estimated shape of the ultrasound beam; p3 refers to a coordinate $(x_3,y_3)$ at a bottom left corner of the estimated shape of the ultrasound beam; p4 refers to a coordinate $(x_4, y_4)$ at a bottom right corner of the estimated shape of the ultrasound beam.

In some cases, the set of keypoints further comprises point p5, which refers to a coordinate $(x_5,y_5)$ at a bottom centre of the estimated shape of the ultrasound beam. In some cases, the processor is configured to execute the instructions to automatically compute within the ultrasound image the set of keypoints by at least: inputting the ultrasound image into a prediction model that predicts at least a subset of values of the set of keypoints.

In some cases, additional values of the set of keypoints are computed based on known relationships between the additional values of the set of keypoints and one or more of the subset of values of the set of keypoints.

In some cases, the prediction model is a neural network model.

In some cases, the neural network model is a deep convolutional neural network and the set of keypoints are a set of regression targets for the deep convolutional neural network. In some cases, a potential range for each one of the regression targets is within an image coordinate space of the ultrasound image. In some other cases, a potential range for each one of the regression targets is within a normalized image coordinate space of the ultrasound image.

In some cases, the neural network model is a vision transformer and the set of keypoints are a set of regression targets for the vision transformer.

In some cases, the processor is configured to execute the instructions to automatically compute within the ultrasound image the set of keypoints by at least inputting the ultrasound image into a prediction model that predicts at least a subset of values of the set of keypoints. In some cases, the subset of values of the set of keypoints comprises $x_1$, $y_1$, $x_2$, $x_3$, $y_3$, and $x_4$. In some cases, the prediction model is a neural network model configured to predict $x_1$, $y_1$, $x_2$, $x_3$, $y_3$, and $x_4$. In some cases, the processor is configured to execute the instructions to further automatically compute $y_2$ and $y_4$ using at least:

Equation 1 comprising $y_1=y_2$; and
Equation 2 comprising $y_3=y_4$.

In some other cases, the subset of values of the set of keypoints comprises $x_1$, $y_2$, $x_2$, $x_3$, $y_4$, and $x_4$, and the prediction model is a neural network that predicts $x_1$, $y_2$, $x_2$, $x_3$, $x_4$, and $x_4$. In some cases, the processor is configured to execute the instructions to further automatically compute $y_1$ and $y_3$ using at least:

Equation 1 comprising $y_2=y_1$; and
Equation 2 comprising $y_4=y_3$.

In some cases, the set of known beam geometries comprises a phased array point geometry, a phased array flat geometry, a curved linear array geometry, and a linear array geometry.

In some cases, the phased array point geometry comprises a region bounded by at least a portion of a circumference of a circle below the region, a left line with a first slope above the portion of the circumference of the circle, a right line with a second slope above the portion of the circumference of the circle, and the left line and the right line intersect at a point above the portion of the circumference of the circle.

In some cases, the phased array point geometry comprises a region bounded by at least a parabola below the region, a left line with a first slope above the parabola, a right line with a second slope above the parabola, and the left line and the right line intersect at a point above the parabola.

In some cases, the phased array flat geometry comprises a region bounded by at least a portion of a circumference of a circle below the region, a left line with a first slope above the portion of the circumference of the circle, a right line with a second slope above the portion of the circumference of the circle, and the left line and the right line intersect at opposite ends of a horizontal top line above the portion of the circumference of the circle.

In some cases, the curved linear array geometry comprises a region bounded by at least a first portion of a circumference of a first circle below the region, a left line with a first slope above the first portion of the circumference of the first circle, a right line with a second slope above the first portion of the circumference of the first circle, and the left line and the right line intersect opposite ends of an second portion of a circumference of a second circle; wherein the second portion of the circumference of the second circle is positioned above the first portion of the circumference of the first circle, and the second portion of the circumference of the second circle and the first portion of the circumference of the first circle have a same orientation.

In some cases, the linear array geometry comprises a rectangular geometry.

In some cases, computing a first determination that $|x_3-x_1|<t_{linear}$ and $|x_4-x_2|<t_{linear}$, wherein $t_{linear}$ is a threshold distance associated with the linear array geometry, then selecting the linear array geometry as the beam geometry.

In some cases, after determining that the first determination is not applicable to the set of keypoints comprising p1, p2, p3, and p4, computing a second determination that $|x_2-x_1|<t_{phased}$, wherein $t_{phased}$ is a threshold distance associated with the phased array point geometry, and then selecting the phased array point geometry as the beam geometry.

In some cases, when $|x_2-x_1|<t_{phased}$, the processor is configured to automatically set $x_2$ and $x_1$ to equal $(x_1+x_2)/2$, to be consistent with the phased array point geometry.

In some cases, after determining that the second determination is not applicable to the set of keypoints, computing a third determination that comprises: computing a region of interest below a horizontal midpoint of p1 and p2; determining that a pixel colour value of the region of interest matches a masking pixel colour value; and selecting the curved linear array geometry as the beam geometry.

In some cases, after determining that the third determination is not applicable to the set of keypoints, the processor is configured to execute the instructions to then selecting the phased array flat geometry as the beam geometry.

In some cases, the processor is configured to execute the instructions to automatically modify the set of keypoints based on the beam geometry to generate the modified set of keypoints that defines the modified shape of the ultrasound beam image by at least: translating at least one of the set of keypoints to generate the modified shape that matches the beam geometry.

In some cases, the processor is configured to execute the instructions to automatically compute the masked ultrasound image using at least the binary mask by at least: computing a Hadamard product of the binary mask and the ultrasound image.

In some cases, the processor is configured to execute the instructions to further: automatically perform optical character recognition on the masked ultrasound image to detect text; and after detecting the text, set pixels of the text to a pixel color matching the binary mask. In some other cases, the processor sets the pixels of the text to black, which may not match the color of the binary mask.

In some cases, the ultrasound image is a given frame in an ultrasound video that comprises a plurality of frames; and the plurality of frames of the ultrasound video are automatically inputted into a neural network model to predict the set of keypoints.

In some cases, the processor is configured to execute the instructions to automatically compute a Hadamard product of the binary mask and each one of the plurality of frames of the ultrasound video to generate a plurality of masked frames that form a masked ultrasound video.

In some cases, the processor is configured to execute the instructions to further: compute a pixel coefficient of variation (CV) across the plurality of masked frames using $CV=\sigma/\mu$, wherein $\sigma$ is a standard deviation of each pixel's intensity across the plurality of frames and $\mu$ is a mean pixel intensity of the masked ultrasound video; identify a set of pixels in the masked ultrasound video as comprising ultrasound data, wherein each pixel in the set of pixels has a CV value above $t_{CV}$, wherein tov is a CV threshold; remove the set of pixels from the masked ultrasound video to produce a plurality of modified intermediate frames of the masked ultrasound video; applying contour detection to one or more edges in each of the modified intermediate frames of the masked ultrasound video to identify one or more pixels as artifacts; and, for each one of the plurality of masked frames of the masked ultrasound video, modify the one or more pixels identified as artifacts to have a same color matching the binary mask.

In another broad aspect, a system is provided for masking an ultrasound video, comprising: a memory storing instructions; and a processor coupled to the memory. The processor is configured to execute the instructions to: automatically compute within the ultrasound video a set of keypoints that define an estimated shape of an ultrasound beam image within the ultrasound video; automatically select, using the set of keypoints, a beam geometry from amongst a set of known beam geometries; automatically modify the set of keypoints based on the beam geometry to generate a modified set of keypoints that defines a modified shape of the ultrasound beam image; automatically compute a binary mask configured to mask pixels around the modified shape of the ultrasound beam image, using at least the modified set of keypoints and the beam geometry; and automatically compute and output a masked ultrasound video by applying the binary mask to each one of a plurality frames of the ultrasound video.

In some cases, a binary mask is produced that applies to all the frames in the ultrasound video and then applies that same binary mask to each frame in the ultrasound video. In this case, the outputs of the prediction model are averaged to produce a set of coordinates that apply to all the frames for the subsequent steps.

According to some aspects, the present disclosure provides a non-transitory computer-readable medium storing computer-executable instructions. The computer-executable instructions, when executed, configure a processor to perform any of the computations and processes described herein.

BRIEF DESCRIPTION OF THE DRAWINGS

The drawings included herewith are for illustrating various examples of articles, methods, and systems of the present specification and are not intended to limit the scope of what is taught in any way. In the drawings.

DETAILED DESCRIPTION

An ultrasound masking computing system and a computing method are provided. In some cases, the ultrasound masking computations are vendor agnostic, or manufacturer agnostic. In some cases, the ultrasound masking computations are applicable to three major types of ultrasound probes, including phased array probes, curved linear probes, and linear probes. In some cases, the ultrasound masking computations deliver beam masks with sharp boundaries, even in dark regions. In some cases, the ultrasound masking computations does not rely on a costly decoder module, as in segmentation solutions. In some cases, the ultrasound masking computations identify cases where text is on the periphery and/or interior of the ultrasound beam image. In some cases, the ultrasound masking computations include predicting the ultrasound probe type.

Figure 1A:
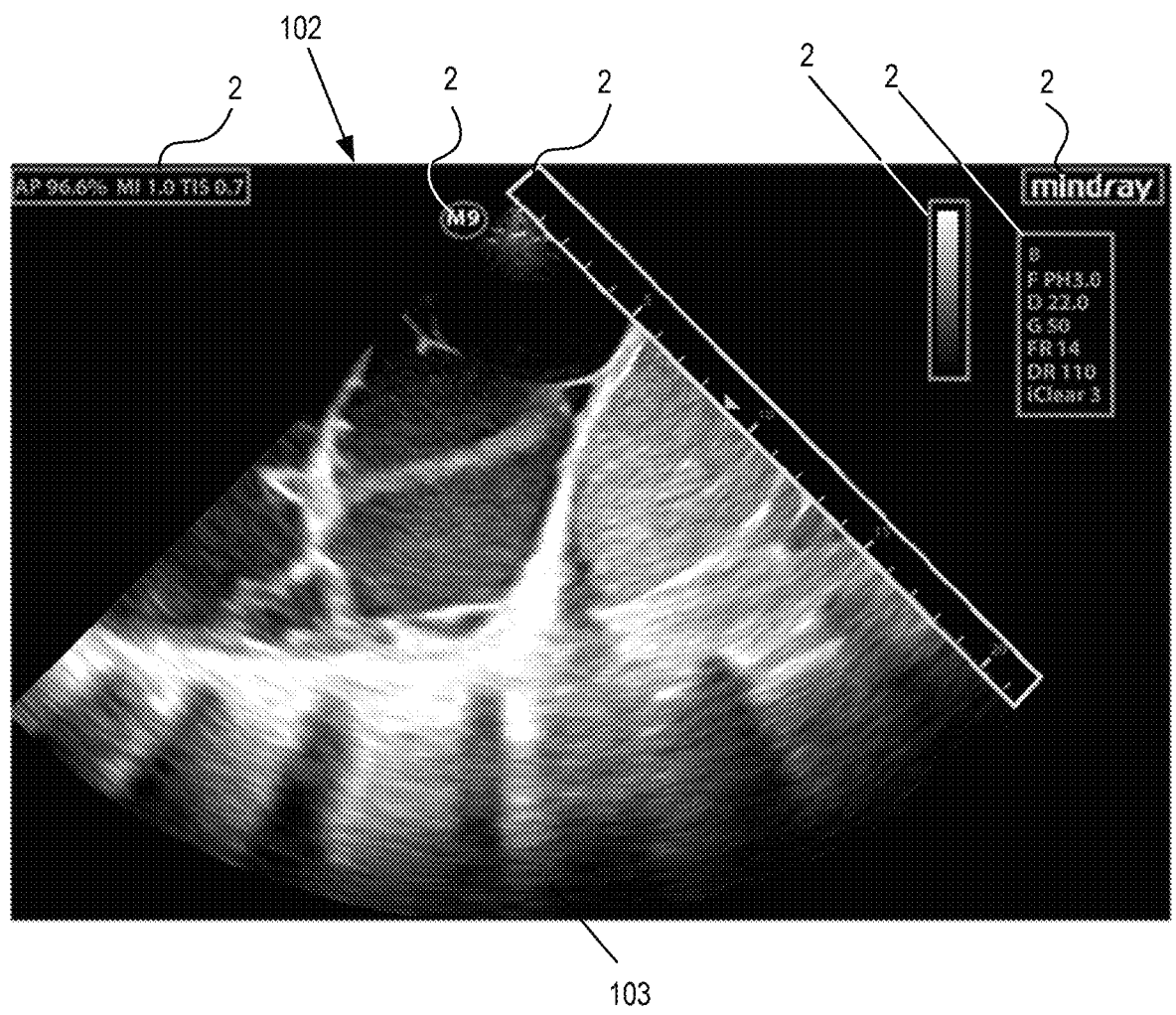
FIG. 1A is a screenshot of a phased array ultrasound image from a first given manufacturer, in accordance with at least some embodiments.
Figure 1B:
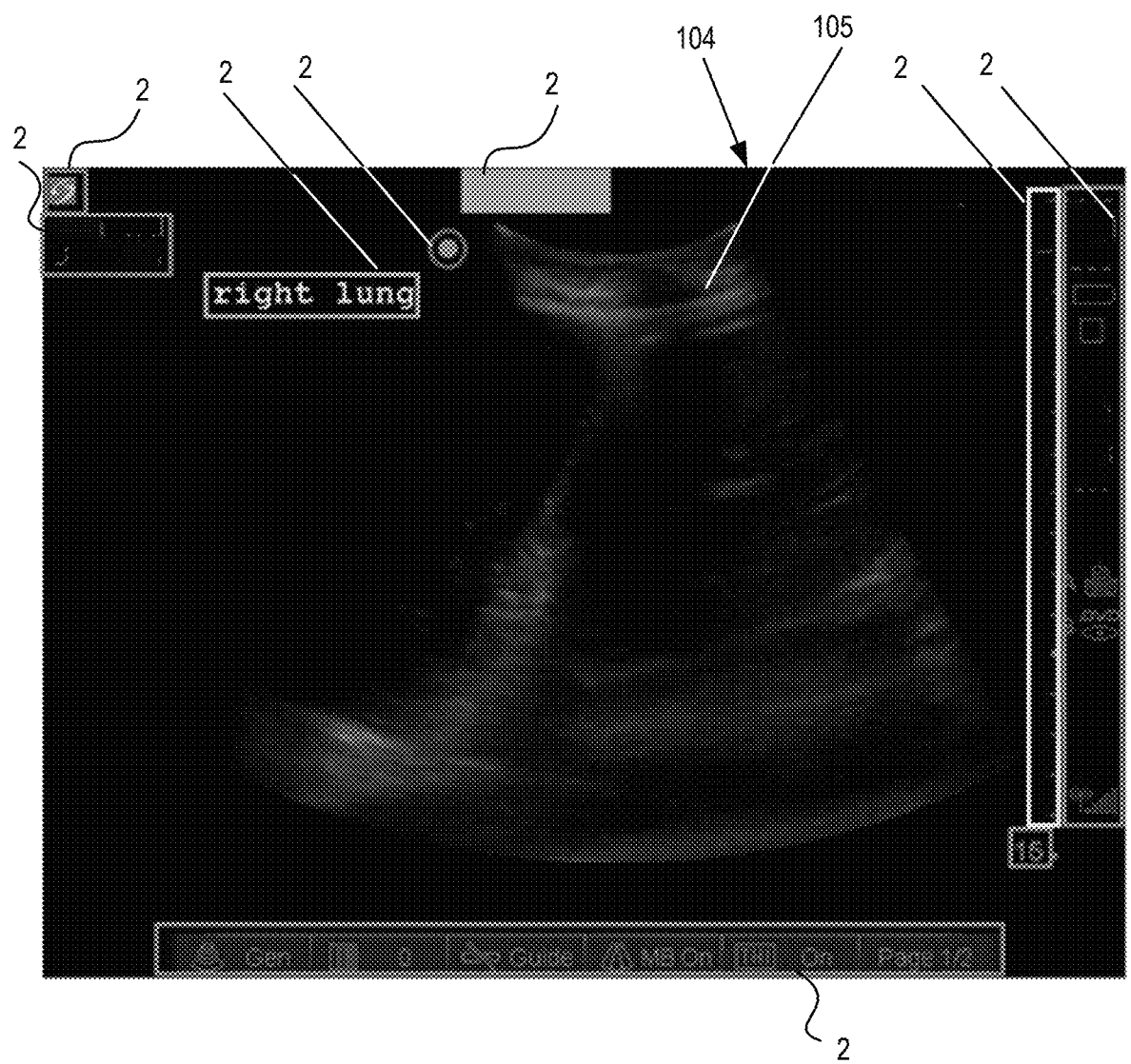
FIG. 1B is a screenshot of a curved linear array ultrasound image from a second given manufacturer, in accordance with at least some embodiments.
Figure 1C:
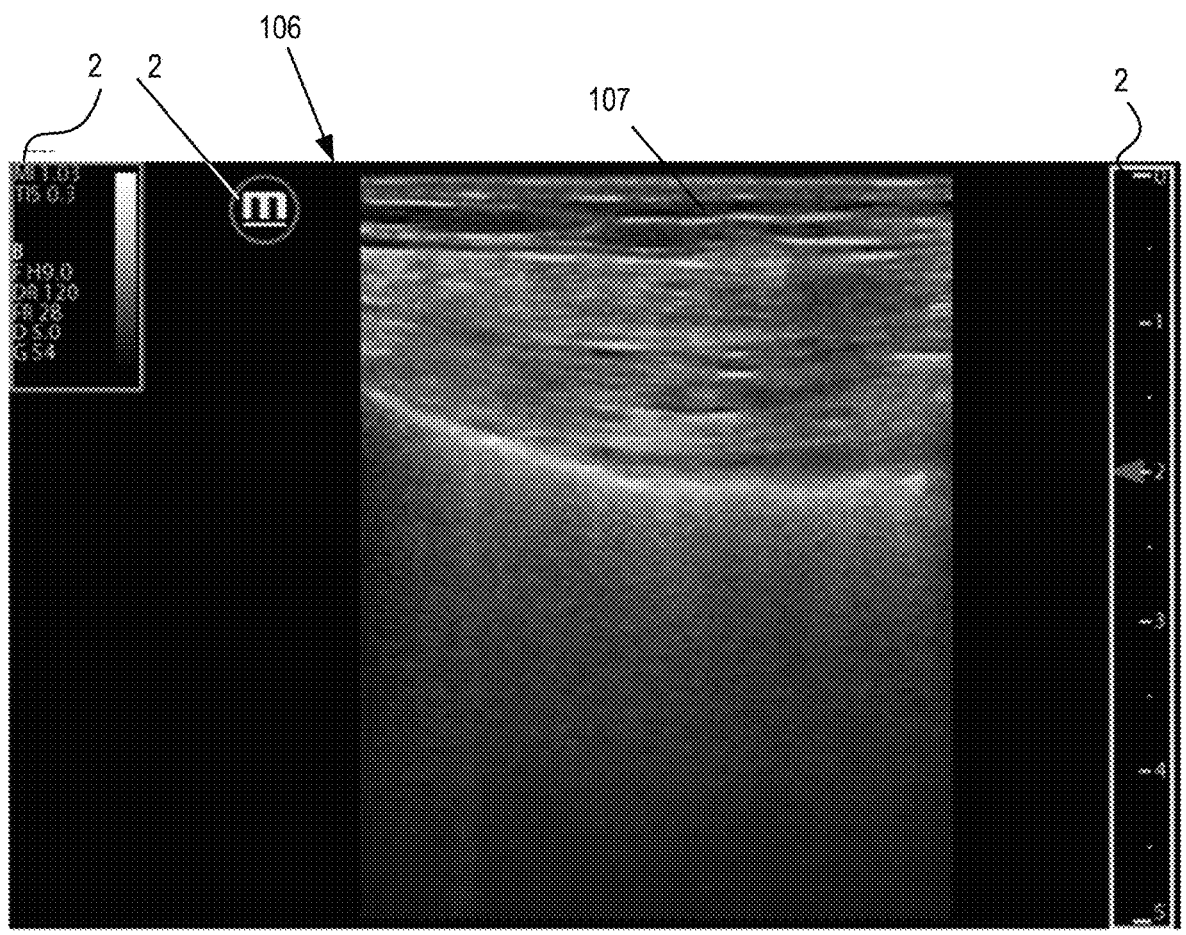
FIG. 1C is a screenshot of a linear array ultrasound image from the first given manufacturer, in accordance with at least some embodiments.
Figure 1D:
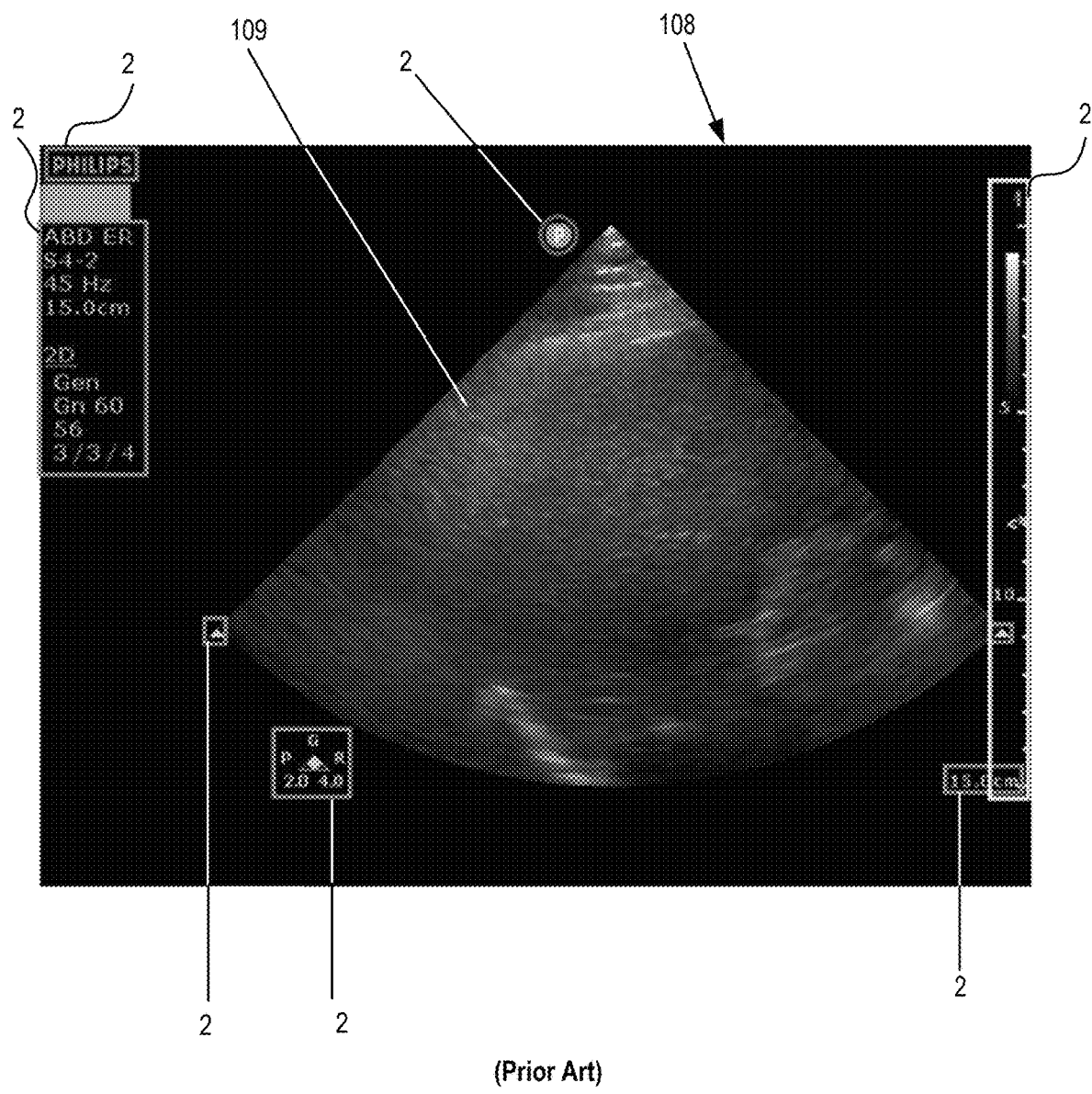
FIG. 1D is a screenshot of a phased array ultrasound image from a third given manufacturer, in accordance with at least some embodiments.
Figure 2:
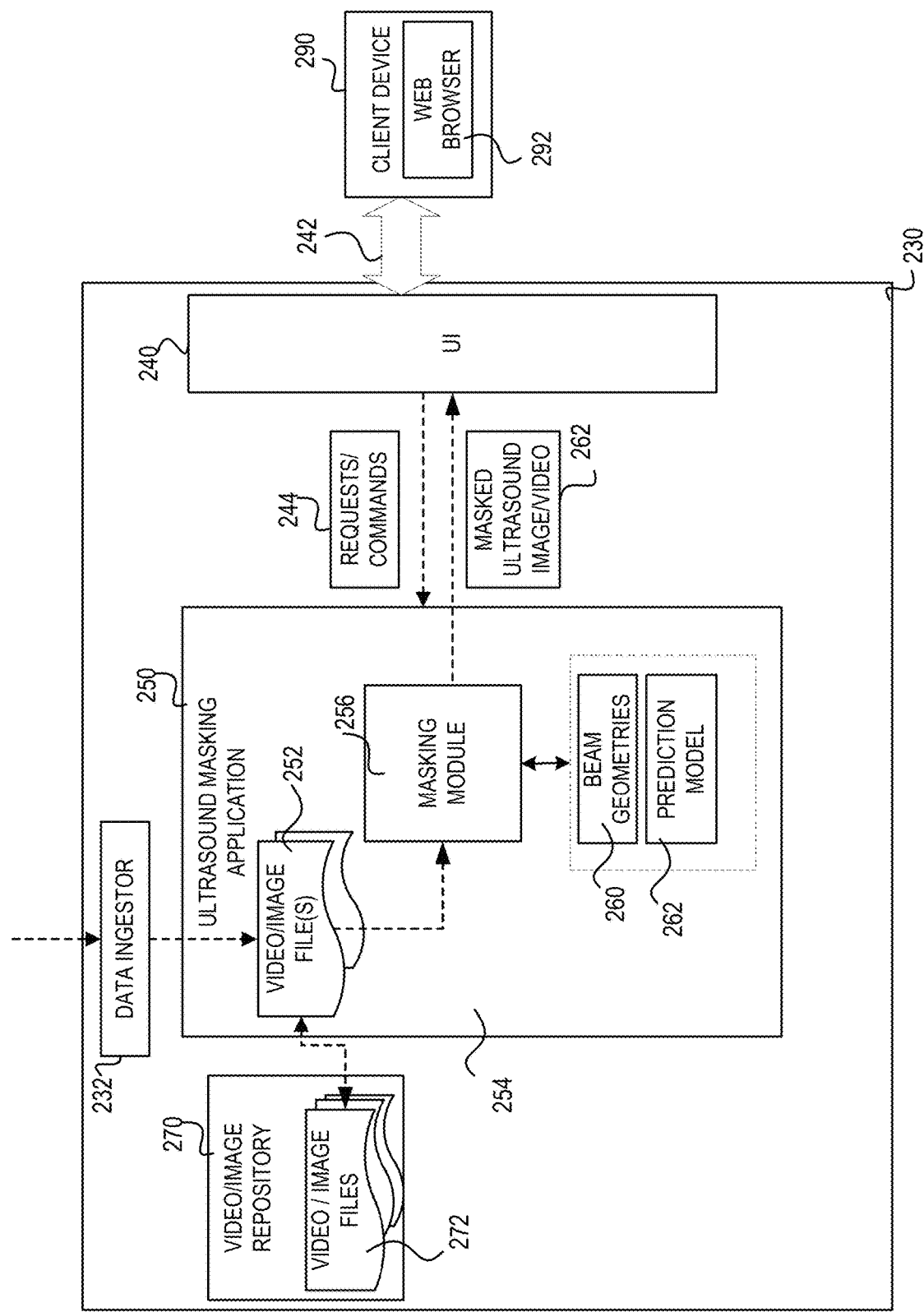
FIG. 2 is a block diagram of a computing system showing software and data components for computing masked ultrasound images or video in accordance with at least some embodiments.

Referring now to FIG. 2, an example of a computing system 230 is shown that is configured 2 execute ultrasound masking computations. The computing system 230 includes an ultrasound masking application 250, a user interface 240 and a video and/or image repository 270 that stores thereon ultrasound video files or image files, or both 272. In some cases, the computing system 230 includes a data ingestor 232 that obtains ultrasound video and/or image files 252, which may be processed directly by the ultrasound masking application 250 or may be stored in the video and/or image repository 270. In other words, in some cases, ultrasound video files or ultrasound images, or both, could be obtained by using the data ingestor 232 or could be obtained from the video and/or image repository 270.

The ultrasound video files or ultrasound images files, or both, 252 are inputted into a masking module 256 of the ultrasound masking application 260. The masking module 256 includes or has access to a library of beam geometries 260 and one or more prediction models 262, which the masking module 256 accesses to process the ultrasound video files or the ultrasound images, or both, and to respectively output masked ultrasound video files or masked ultrasound image files, or both 262.

In some cases, the masked ultrasound video files or masked ultrasound image files, or both 262 are outputted to a user interface (UI) module 240 that is displayable on a client device 290, such as a web browser 292 that operates on the client device 290.

In some cases, the client device 290 sends requests or commands 244 to the UI module 240 via a communication link 242 (e.g., a network link) and the requests or commands 244 are transmitted to the ultrasound masking application 250. In some cases, the requests or commands 244 include initiating masking of selected ultrasound video files or selected ultrasound images files, or both.

In some cases, the library of beam geometries 260 includes mathematical relationships of keypoints associated with each type of beam geometry. In some cases, the beam geometries include: a phased array (flat); a phased array (point); a curved linear array; and a linear array.

In some cases, the prediction model 262 is a neural network model. In some cases, the neural network model is a deep convolutional neural network and a set of keypoints are a set of regression targets for the deep convolutional neural network. In some other cases, the neural network model is a variant of a vision transformer and a set of keypoints are a set of regression targets for the vision transformer. In some cases, a vision transformer (ViT) breaks down an input image into a series of patches, serializes each patch into a vector, and maps it to a smaller dimension with matrix multiplication. The vectors are processed by a transformer encoder. In some other cases, a variant of vision transformers is used in the prediction model 262. Examples of variants of vision transformers include masked autoencoder, switch transformer, and VIT-VQGAN. In VIT-VQGAN, processes similar to a vector quantized (VQ) variational encoder and generative adversarial network (GAN) are incorporated into the vision transformer. It will be appreciated that other currently known and future known vision transformers may be applicable to the principles described herein, including being applied in the prediction model 262 to compute the set of keypoints.

The computing system 230 is an example embodiment. In some cases, the computing system 230 is a server machine. In some other cases, the computing system 230 is a desktop computer. In some other cases, the computing system 230 is a virtual machine instantiated as a processing node on a cloud computing platform. Other computing architectures for computing ultrasound masking could be used.

Figure 3:
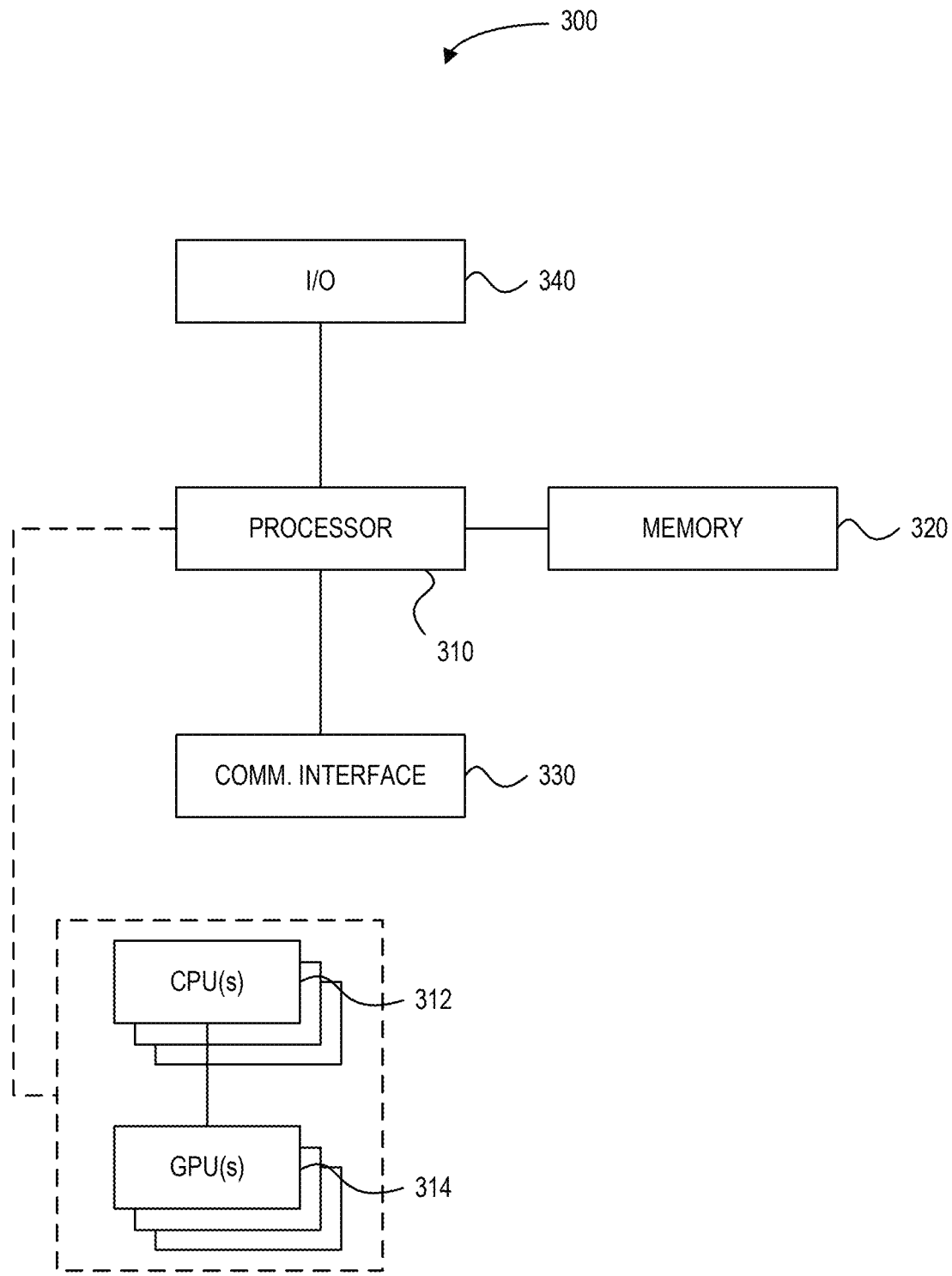
FIG. 3 is a schematic block diagram of a computer in accordance with at least some embodiments.

Referring now to FIG. 3, there is illustrated a simplified block diagram of a computer in accordance with at least some embodiments. Computer 300 is an example implementation of the computing system 230 or client device 290, or both, of FIG. 2. Computer 300 has at least one processor 310 operatively coupled to at least one memory 320, at least one communications interface 330 (also herein called a network interface), and at least one input/output device 340.

The at least one memory 320 includes a volatile memory that stores instructions executed or executable by processor 310, and input and output data used or generated during execution of the instructions. Memory 320 may also include non-volatile memory used to store input and/or output data—e.g., within a database—along with program code containing executable instructions.

Processor 310 may transmit or receive data via communications interface 330, and may also transmit or receive data via any additional input/output device 340 as appropriate.

In some cases, the processor 310 includes a system of central processing units (CPUs) 312. In some other cases, the processor includes a system of one or more CPUs and one or more Graphical Processing Units (GPUs) 314 that are coupled together. For example, the masking module 256 executes machine learning computations for the prediction module 262 on CPU and GPU hardware, such as the system of CPUs 312 and GPUs 314.

Beam Geometries

In some cases, a vendor-agnostic computing system is provided to remove extraneous entities (also herein called artifacts) from ultrasound images that is configured for several types of ultrasound probes.

Figure 4A:
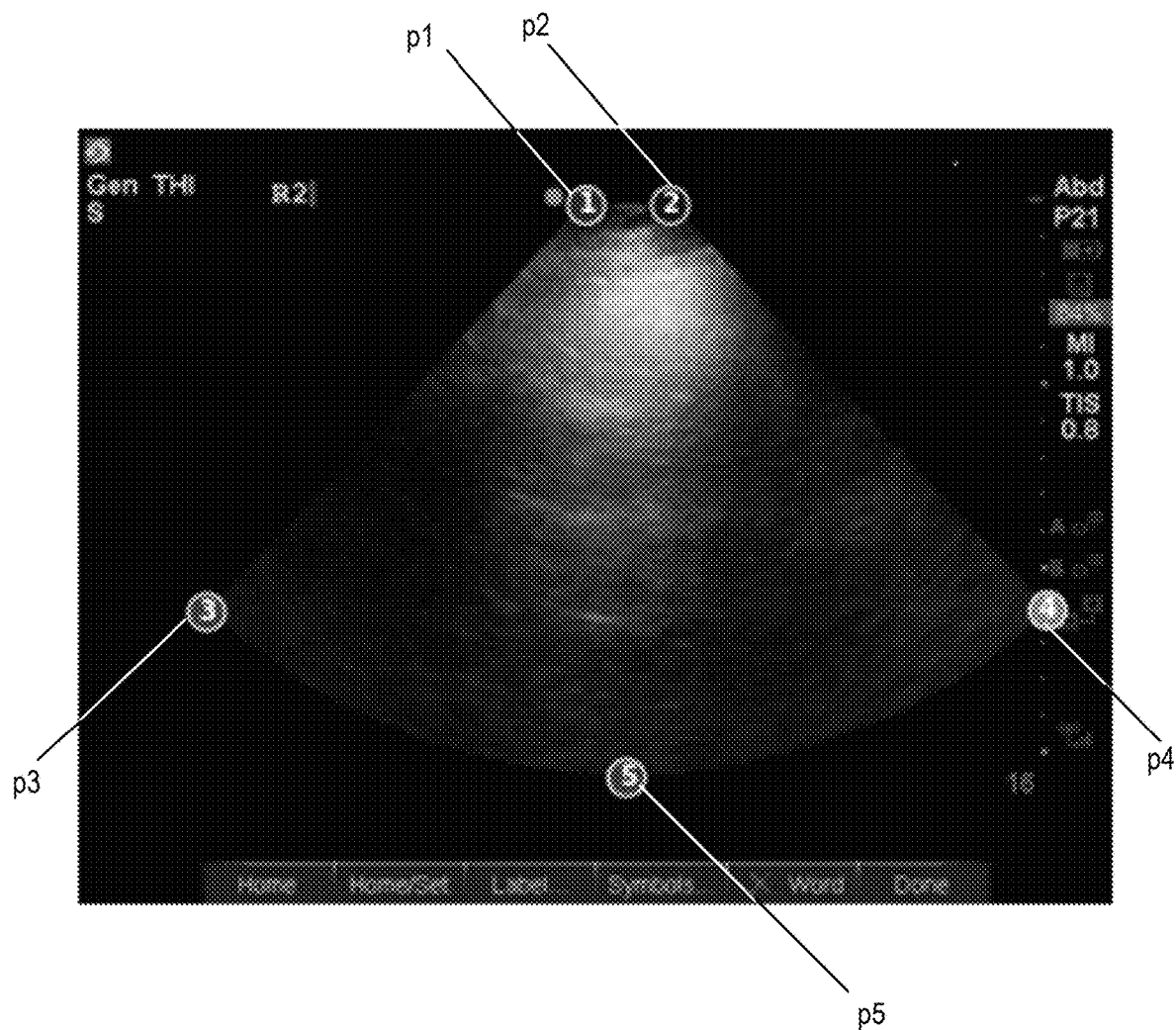
FIG. 4A is a screenshot of a phased array (flat) ultrasound image showing keypoints in accordance with at least some embodiments.
Figure 4B:
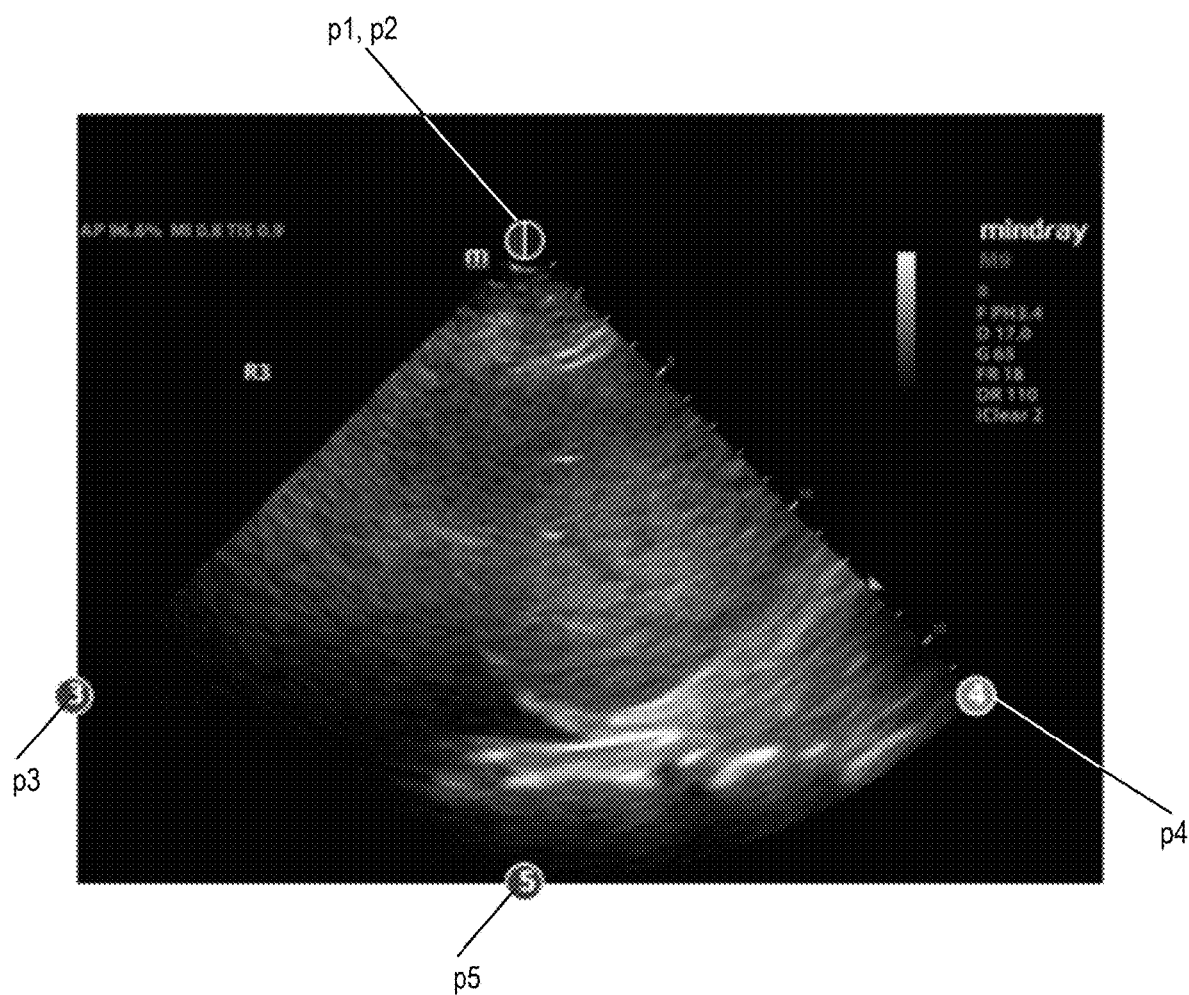
FIG. 4B is a screenshot of a phased array (point) ultrasound image showing keypoints in accordance with at least some embodiments.
Figure 4C:
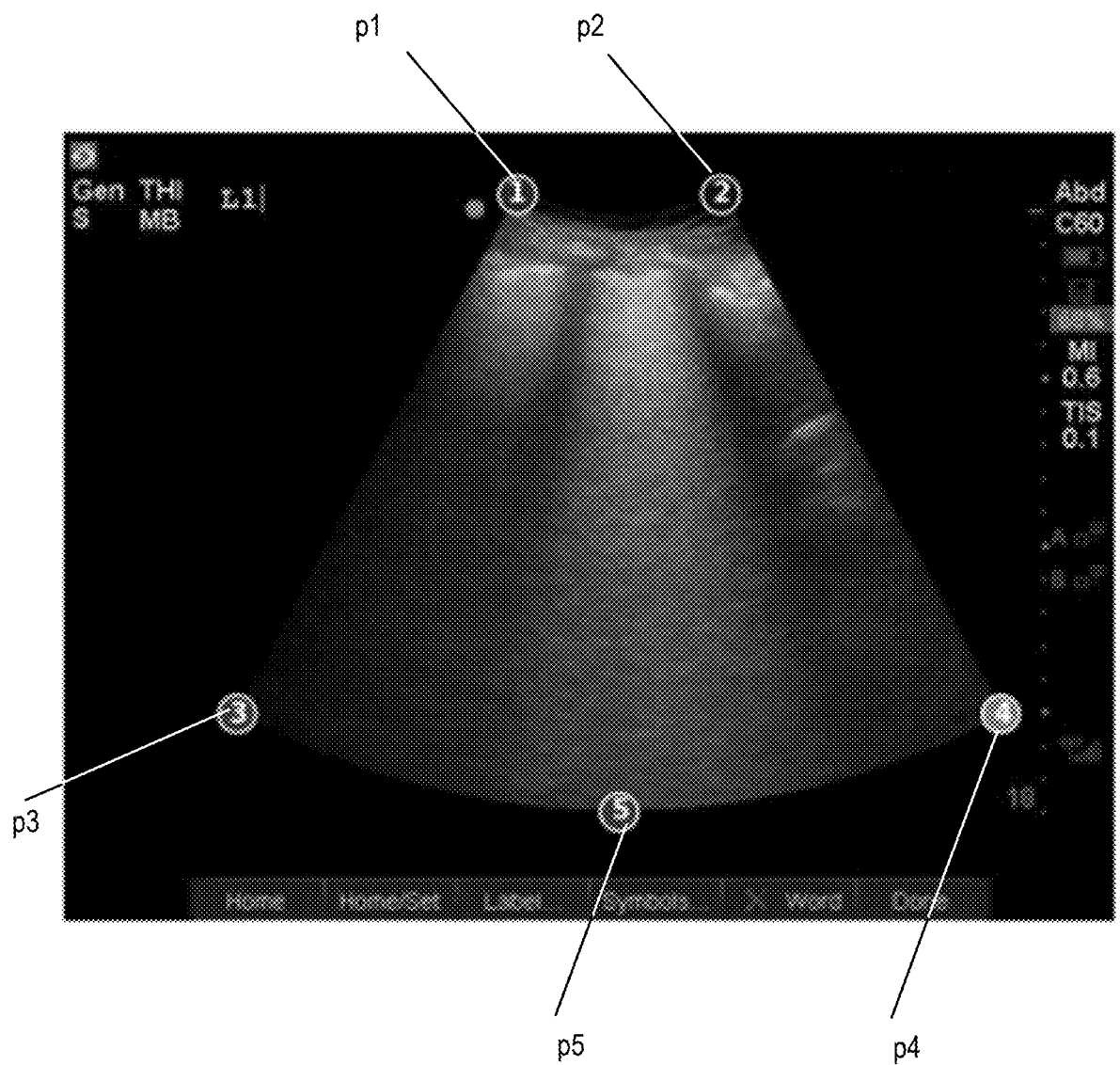
FIG. 4C is a screenshot of a curved linear array ultrasound image showing keypoints in accordance with at least some embodiments.
Figure 4D:
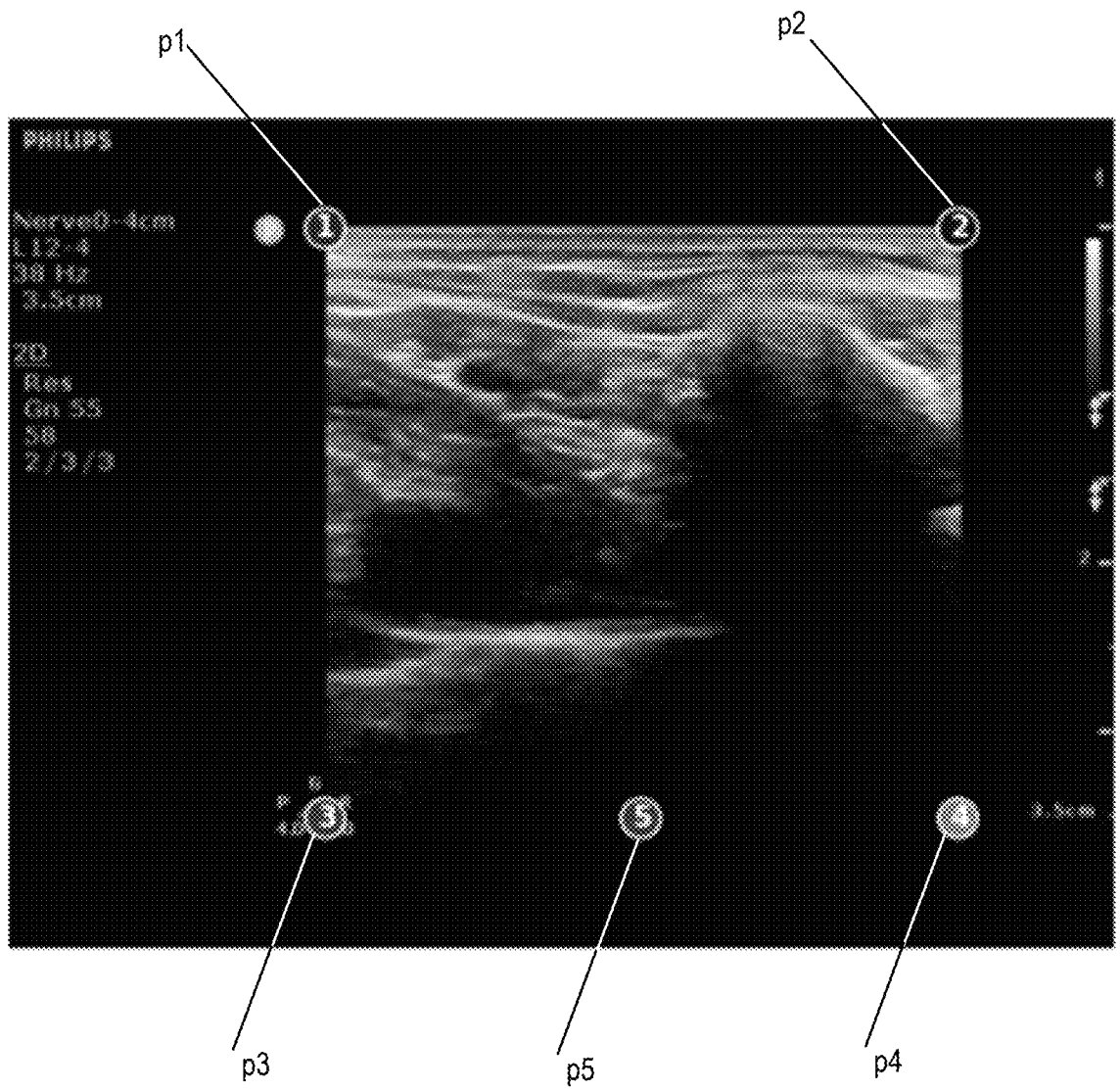
FIG. 4D is a screenshot of a linear array ultrasound image showing keypoints in accordance with at least some embodiments.

The method described herein was designed to accept input ultrasound images captured by the following major probe types: (i) a phased array (see FIGS. 4A and 4B), a curved linear array (see FIG. 4C), and a linear array (see FIG. 4D). Beams produced by each probe type correspond to a geometric form that can generally describe all beams produced by that particular probe type. Although all beams of a particular probe type are oriented the same direction and are vertically symmetrical, several aspects of the beam differ across manufacturers and device settings. The position, width, height, and scale of the beam depend on several acquisition-related factors such as vendor and depth. It will be appreciated that the processes described herein could be applied to other beam shapes. For example, ultrasound device vendors and manufacturers could later develop other beam geometries, and the ultrasound image masking process described herein may be applied to future-known beam geometries.

Hereafter, keypoints refer to pixel positions that each have a x and a y coordinate pair. The keypoints are used to geometrically identify the beams. In some cases, four keypoints p1, p2, p3, are used p4 to identify the beam geometry. In some cases, the keypoints p1, p2, p3, p4, and p5 are used. In some other cases, there are even more than five keypoints used to identify the beam geometry. In some other cases, three keypoints are used to identify the beam geometry.

The keypoint p1 refers to the top left corner of an ultrasound beam image; the keypoint p2 refers to a top right corner of the ultrasound beam image; the keypoint p3 refers to a bottom left corner of the ultrasound beam image; and the keypoint p4 refers to a bottom right corner of the ultrasound beam image. In cases that include a fifth keypoint, the keypoint p5 refers to a bottom centre of the ultrasound beam image.

A given keypoint is denoted as $pi=(x_i, y_i)$ and makes reference to the x- and y-coordinates of keypoints. As applicable to the different beam geometries, $x_5$ is the horizontal centre of the beam. Note that the centre of the beam is not necessarily the centre of the image. Moreover, the relationships in Equations 1, 2, and 3 hold for all probe types, which also includes the different beam geometries.

$$y_1 = y_2 \quad \text{Equation 1:}$$

$$y_3 = y_4 \quad \text{Equation 2:}$$

$$x_5 = (x_1+x_2)/2 = (x_3+x_4)/2 \quad \text{Equation 3:}$$

In some cases, a normalized image coordinate space is herein used, where (0, 0) refers to the top left corner of an image and (1, 1) is the bottom right corner of the image.

Phased Array: In some cases, a region is bounded below by a portion of a circumference of a circle, and above by three lines. The portion of the circumference of the circle intersects the keypoints p3 and p4. The left line has a negative slope (in image coordinate space) and it intersects keypoints p1 and p3. The right line has a positive slope and it intersects p2 and p4. More generally, the left boundary line and the right boundary line have opposite angled slopes that slope towards each other in one direction, and slope away from each other in an opposite direction. A horizontal line intersecting p1 and p2 bounds the beam from above (see FIG. 4A), which in some cases is called a phased array (flat). In some other cases, the left and right lines intersect at a point at the top of the beam, rendering the length of the horizontal line 0 (FIG. 4B); such cases are referred to as phased array (point).

In some cases, the portion of the circumference of a circle is an approximation for a curve representing a bottom boundary of the beam. In other words, in some cases, the bottom of boundary of the beam is formed as an arc of a circle. The point of intersection of the two lateral linear bounds can be used to calculate the radius of the circle, which may in turn be used to determine the circle's equation. This alternative scheme would use knowledge of keypoints p1, p2, p3, and p4.

In some other cases of a phased array, instead of using a circle to approximate the bottom boundary layer of the beam, a parabola is used to compute the bottom boundary layer of the beam. The parabola is defined using the keypoints p3, p4 and p5, whereby p5 is positioned horizontally midway between p3 and p4. The x-coordinate of the intersection of the negative sloped left line and the positive sloped right line is $x_5$. The keypoint p5 is the parabola's maximum in a typical image space. In some cases of an image space, the top left corner of an image is the origin having the pixel coordinates (0,0) and the x-coordinates increase in the rightward direction while the y-coordinates increase in the downward direction. Similarly, a horizontal line intersecting p1 and p2 bounds the beam from above (see FIG. 4A), which in some cases is called a phased array (flat). In some other cases, in which the left and right lines intersect at a point at the top of the beam, rendering the length of the horizontal line 0 (FIG. 4B), these cases are referred to as phased array (point).

Curved linear (a.k.a. curvilinear) array: The beam is a region defined by an upper boundary of the beam that is shaped as a positive oriented portion of a circumference of a first circle (e.g., called an upper circle arc) and a bottom boundary of the beam that is shaped as a positive oriented portion of a circumference of a second circle (e.g., called a lower circle arc), and the beam is furthered defined by two lines connecting the upper circle arc to the lower circle arc on both sides of the beam. More generally, the upper circle arc and the lower circle arc are both oriented in the same direction. The lower circle arc intersects p3 and p4. The upper circle arc intersects p1 and p2. In some cases, the computing system does not solve for the minimum of the upper parabola, because that the region between p1 and p2 is always set to black. As such, the beam masking detection problem is simplified for the curved linear array geometry. As in phased array probe types, the left boundary is a line with a negative slope that intersects p1 and p3, while the right boundary is a line with has a positive slope that intersects p2 and p4. More generally, the left boundary line and the right boundary line have opposite angled slopes that slope towards each other in one direction, and slope away from each other in an opposite direction. Note that the above formulation is also valid for intracavitary probes.

In some other cases, the upper boundary of the curved linear array beam is defined as a positive oriented parabola (e.g., called an upper parabola) and the bottom boundary of the beam is defined as a positive oriented parabola (e.g., called a lower parabola), and the beam is furthered defined by two lines connecting the upper parabola to the lower parabola on both sides of the beam. The lower parabola intersects p3, p4, and p5, and p5 is its minimum. The upper parabola intersects p1 and p2. Its (unnamed) minimum shares the same x-coordinate as p5. In some cases, the computing system does not solve for the minimum of the upper parabola, because it is assume that the region between p1 and p2 is always set to black. As in phased array probe types, the left boundary is a line with a negative slope that intersects p1 and p3, while the right boundary is a line with has a positive slope that intersects p2 and p4. Note that the above formulation is also valid for intracavitary (a.k.a. endocavitary) probes.

Linear array: The computing system characterizes the beam as a rectangular region whose edges are parallel to the edges of the image. The upper, right, bottom, and left edges are the line segments connecting p1 and p2, p2 and p4, p3, and p4, and p1 and p3 respectively. In some cases, although the presence of p5 is not necessary to represent the beam's shape, it is set to the midpoint of the bottom line segment.

Masking Process

The objective of the masking process is to remove (i.e., "mask out") all text and graphical entities that are present in an ultrasound video and that do not intersect the ultrasound beam. We define a mask as a matrix $M \in \{0, 1\}^{h \times w}$ how that corresponds to an image with width w and height h. Values of the mask set to 1 correspond to pixels within the bounds of the ultrasound beam. Values of the mask set to 0 correspond to pixels extraneous to the ultrasound beam that should be removed (set to black). To remove burnt-in graphical entities that are not contained within the ultrasound beam, the Hadamard product $M \odot /is$ computed for each image/in the ultrasound video. In modern scientific computing libraries, the masking operation may be efficiently computed for the entire video by broadcasting the Hadamard operation across all frames of the video. In most circumstances, the bounds of the ultrasound beam do not change between frames in the same ultrasound video. Hence, it suffices to produce a single two-dimensional mask specifying the pixels constituting the beam that is valid for each image in an entire ultrasound video. If it is uncertain whether the ultrasound beam remains constant throughout the duration of a video, then frame-specific masks can be applied.

In some cases, the observation that the shape of the ultrasound beam can be determined for a variety of probe types when the positions of a select few named keypoints are known. As outlined in the previous section, localizing four named keypoints is sufficient to capture the shapes of the three major probe types. Hence, the major challenge in producing ultrasound beam masks is keypoint localization. The computing system uses a deep learning approach to the problem, treating the keypoints as regression targets for a convolutional neural network. Then, given the four keypoints, the computing system estimates the probe type and make further refinements to tighten the boundaries of the mask, reducing the chances of missing graphics positioned near the beam.

Figure 5:
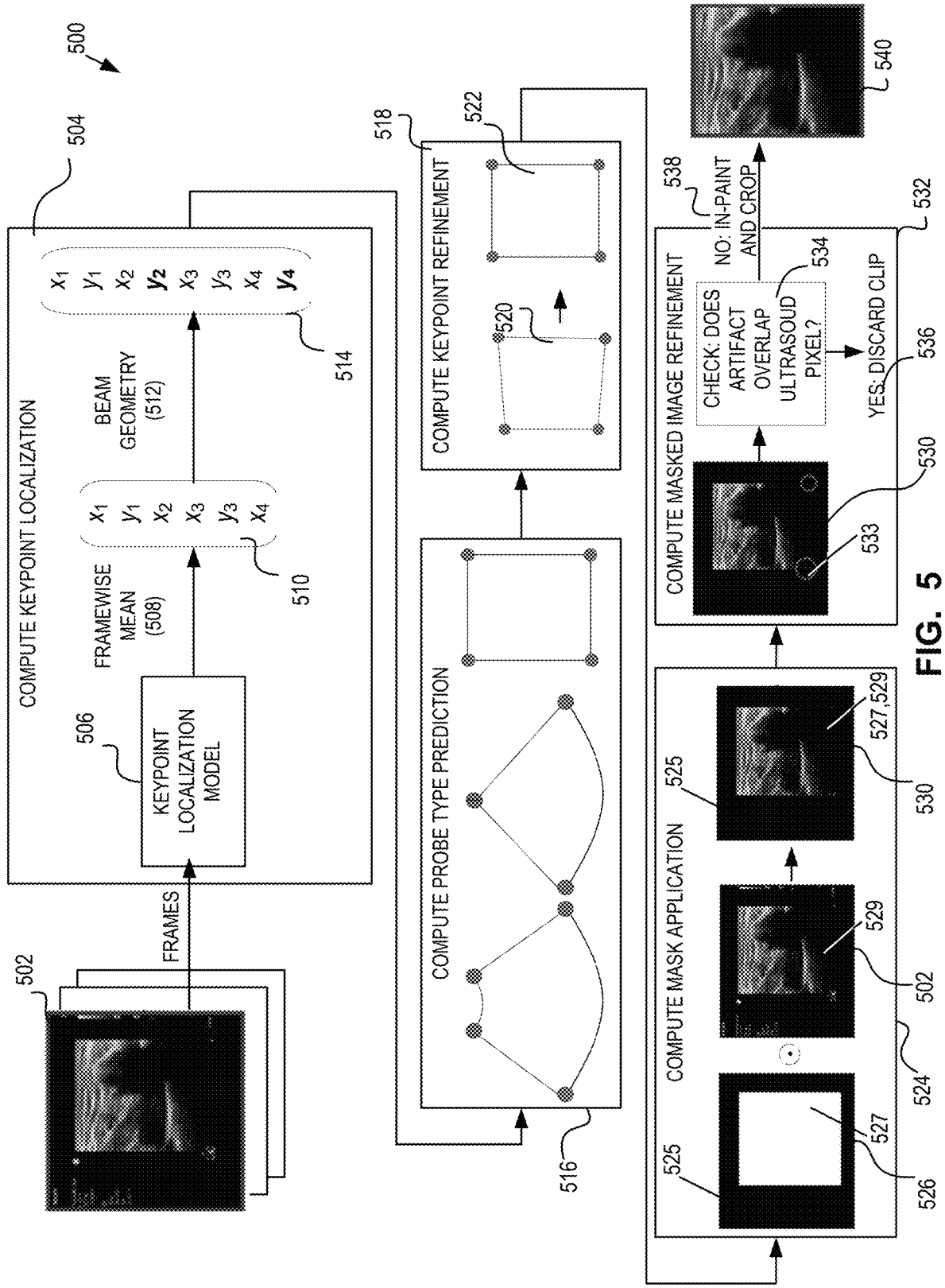
FIG. 5 is a flowchart diagram of an example method of computing masked ultrasound images using four keypoints in accordance with at least some embodiments.

Referring to FIG. 5, in some cases, the computations of the masking process are summarized as follows.

Block 502: Ultrasound video frames or an ultrasound image is inputted into a keypoint localization computation.

Block 504: The keypoint localization computation includes using a trained neural network keypoint localization model 506 to predict keypoints that define the shape of the beam (p1, p2, p3, and p4) in the video. In some cases, an additional keypoint p5 is used to further define the ultrasound beam. In some cases in which there are multiple frames for an ultrasound video, the keypoint localization computation includes computing a mean prediction 508 across all the frames in ultrasound video.

In some cases, a subset of the keypoint coordinate values 510 are predicted. In some cases, the predicted subset of keypoint values 510 include: $x_1, y_1, x_2, x_3, y_3, x_4$. Stored beam geometry relationships 512 are used to then compute $y_2$ and $y_4$. In some cases, the stored beam geometry relationships 512 include $y_2 = y_1$ and $y_4 = y_3$. In some other cases, the predicted subset of keypoint values 510 include $x_1, y_2, x_2, x_3, y_4, x_4$, and the stored beam geometry relationships 512 are used to then compute $y_1$ and $y_3$, which include $y_1 = y_2$ and $y_3 = y_4$. The resulting predicted keypoints p1, p2, p3, p4 in some cases are represented by their coordinates 514: $x_1, y_1, x_2, y_2, x_3, y_3, x_4, y_4$.

In some other cases, the predicted subset of keypoint values could be different depending on the nature of the mathematical relationships amongst the keypoints. For example, in some other cases, a similar model that only works for linear ultrasound clips, which have a rectangular geometry. In such a case, the following stored beam geometry relationships would include: $x_1 = x_3, x_2 = x_4, y_1 = y_2$, and $y_3 = y_4$, and the prediction model is configured to predict only four values (e.g., $x_1, x_2, y_1$, and $y_3$; or $x_3, x_4, y_2$, and $y_4$).

Block 516: The computing system computes a probe type prediction used to capture the ultrasound beam. This includes inputting the ultrasound video frame of the ultrasound image and the predicted keypoints p1, p2, p3, p4 into the prediction model 262, which will then select one of the probe types defined by ultrasound beam geometries, including: a phased array and a linear array. As noted above, in some cases, the phased array could be a phased array (flat) type or a phased array (point) type. In some cases, the linear array could be a curved linear array.

Block 518: The computing system computes a keypoint refinement. In some cases, based on the probe type, the computing system modifies the keypoints based on known geometrical properties for the ultrasound beam geometry. For example, the initially beam geometry 520 has predicted keypoints 514 that may be slightly misaligned. Using the geometric properties for the predicted beam geometry, the predicted keypoints 514 (and more specifically their coordinate values) are adjusted or refined to accurately match the predicted beam geometry 522. The adjusted or refined predicted keypoints are also herein referred to as refined keypoints.

Block 524: The computing system computes a mask application. This includes constructing a binary mask image 526 for the ultrasound beam using the refined keypoints and the predicted beam geometry 522. The binary mask image 526 has the same width and height of the ultrasound video frames or the ultrasound image.

In some cases, the binary mask image 526 is constructed as a Boolean tensor and the binary mask image includes pixels that form an ultrasound image region 527 that is defined by or corresponds to the predicted beam geometry 522. A Boolean tensor is a tensor that assumes binary values and in some cases is endowed with Boolean algebra. In some cases, the computing system designates all pixels bounded by the bottom beam boundary, the left beam boundary, the right beam boundary and the top beam boundary to be part of the ultrasound image region 527. The binary mask image also comprises mask pixels, which in some cases are black, that surround the ultrasound image region 529. The mask pixels form the mask region 525. While the examples show the binary mask color is black, in some cases, a different color is used for the binary mask.

The binary mask image 526 is applied to the inputted ultrasound video frames or the ultrasound image 502, which respectively results in a plurality of masked ultrasound video frames or a masked ultrasound image 530. In some cases, a given masked ultrasound video frame or a given masked ultrasound image 530 includes an ultrasound image region 529 defined by the predicted beam geometry 522, which corresponds in position and shape to the ultrasound image region 527 of the binary mask image 526, and the given masked ultrasound image 530 further includes the mask region 525 that surrounds the ultrasound image region 529.

In some cases, the application of the binary mask image 526 is a Hadamard product between the binary mask image 526 and the inputted ultrasound video frames or the ultrasound image 502, resulting in a plurality of masked ultrasound video frames or a masked ultrasound image 530.

Block 532: The computing system computes a masked image refinement. In some cases, the masked ultrasound image 530 includes artifacts 533, such as pixels that are of a different color other than black (e.g., white or some other color). In some cases, the computing system checks for any regions with remaining text or graphical entities that are brighter than the ultrasound beam and sets the pixels to black. The computing system then determines if any such regions overlap with the beam. If so, an artifact is considered to overlap an ultrasound image pixel, which is a pixel of the ultrasound image region 529. More generally, the computing system determines if an artifact overlaps an ultrasound image pixel, which is a pixel in the ultrasound image region 529. If there is an overlap, the computing system raises a flag indicating that the ultrasound beam likely contains burnt-in artefacts. In some cases, the ultrasound video clip (which includes a plurality of ultrasound video frames) or the ultrasound image is discarded (operation 536). If there are no artifacts that overlap any of the ultrasound image pixels (e.g. the artifacts are not positioned in the ultrasound image region 529), then the computing system proceeds to compute a crop of the ultrasound image region 529 (operation 538) to output a plurality of cropped ultrasound video frames in the case of an inputted video clip, or to output a cropped ultrasound image 540 in the case of an inputted ultrasound image.

The example embodiment shown in FIG. 5 shows a linear array geometry. However, in other cases, other beam geometries could be used, such as a phased array (flat) geometry, a phased array (point) geometry, and a curved linear array geometry.

Figure 6:
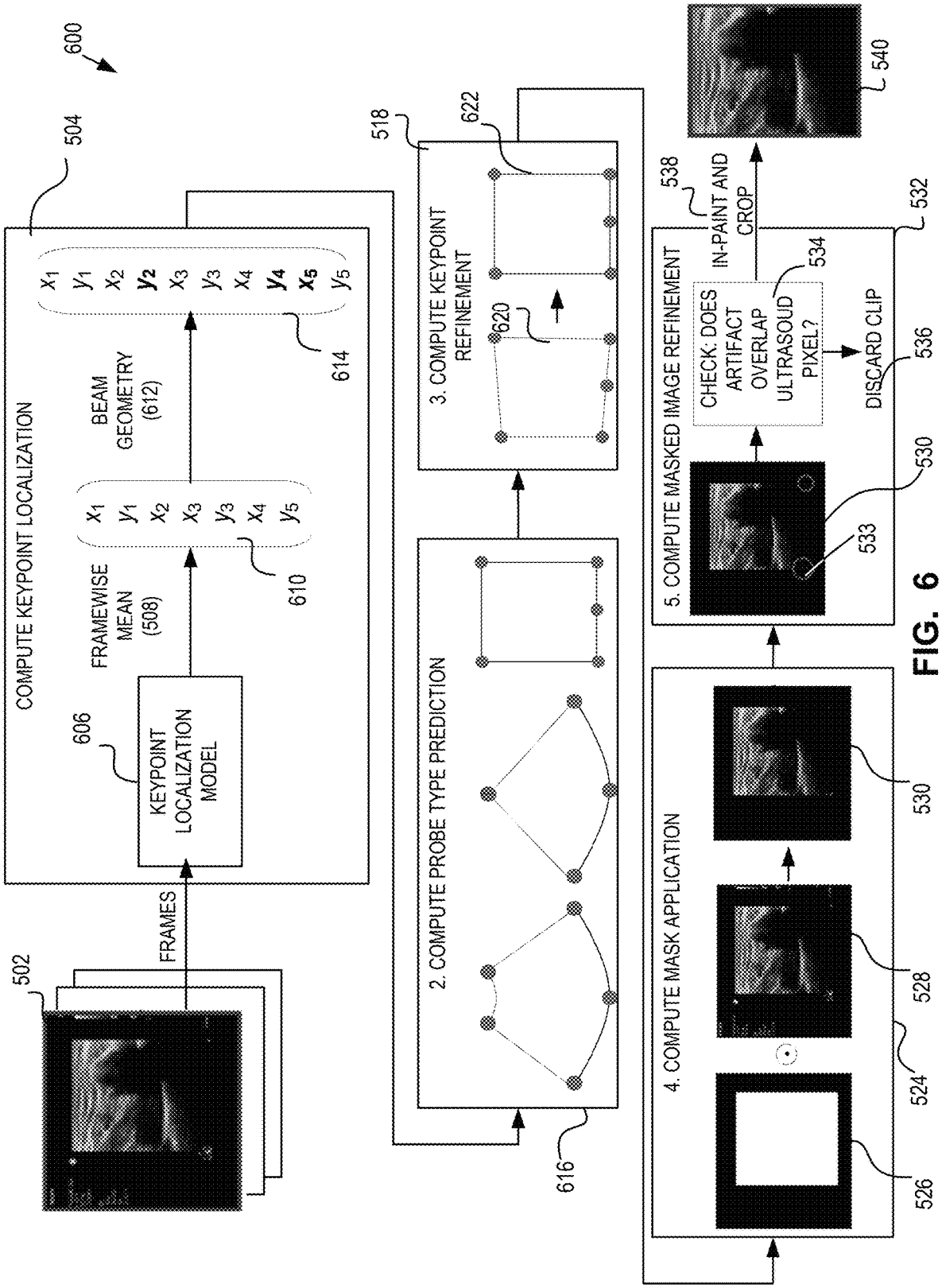
FIG. 6 is a flowchart diagram of an example method of computing masked ultrasound images using five keypoints in accordance with at least some embodiments.

Referring to FIG. 6, in another case, another ultrasound image masking process 600 is shown that is similar to the process 500 in FIG. 5, but an additional keypoint p5 is used. In particular, another keypoint localization model 606 is used to compute a predicted subset of values 610: $x_1$, $y_1$, $x_2$, $x_3$, $y_3$, $x_4$, $y_5$. Beam geometry 612 is used to also calculate $x_5$, which from the x and y coordinates set 614 that corresponding to p1, p2, p3, p4 and p5. A probe type prediction 616 uses the five keypoints. The five keypoints 620 are also refined to generate a refined set of keypoints 622.

Figure 7:
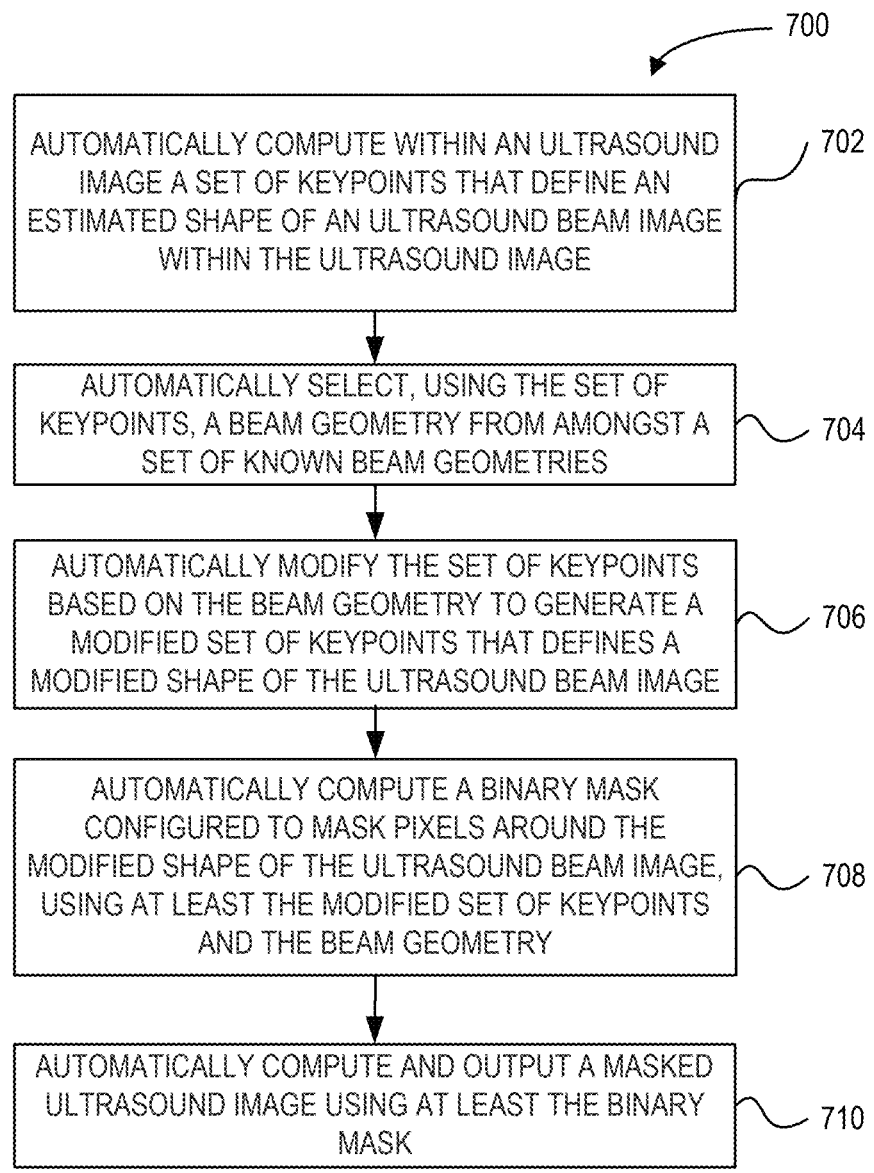
FIG. 7 is a flowchart diagram of an example method of computing a masked ultrasound image in accordance with at least some embodiments.

Referring to FIG. 7, an example computational method 700 is provided for computing a masked ultrasound image.

Block 702: Automatically compute within the ultrasound image a set of keypoints that define an estimated shape of an ultrasound beam image within the ultrasound image.

Block 704: Automatically select, using the set of keypoints, a beam geometry from amongst a set of known beam geometries.

Block 706: Automatically modify the set of keypoints based on the beam geometry to generate a modified set of keypoints that defines a modified shape of the ultrasound beam image.

Block 708: Automatically compute a binary mask around the modified shape of the ultrasound beam image using at least the modified set of keypoints and the beam geometry.

Block 710: Automatically compute and output a masked ultrasound image using at least the binary mask.

Figure 8:
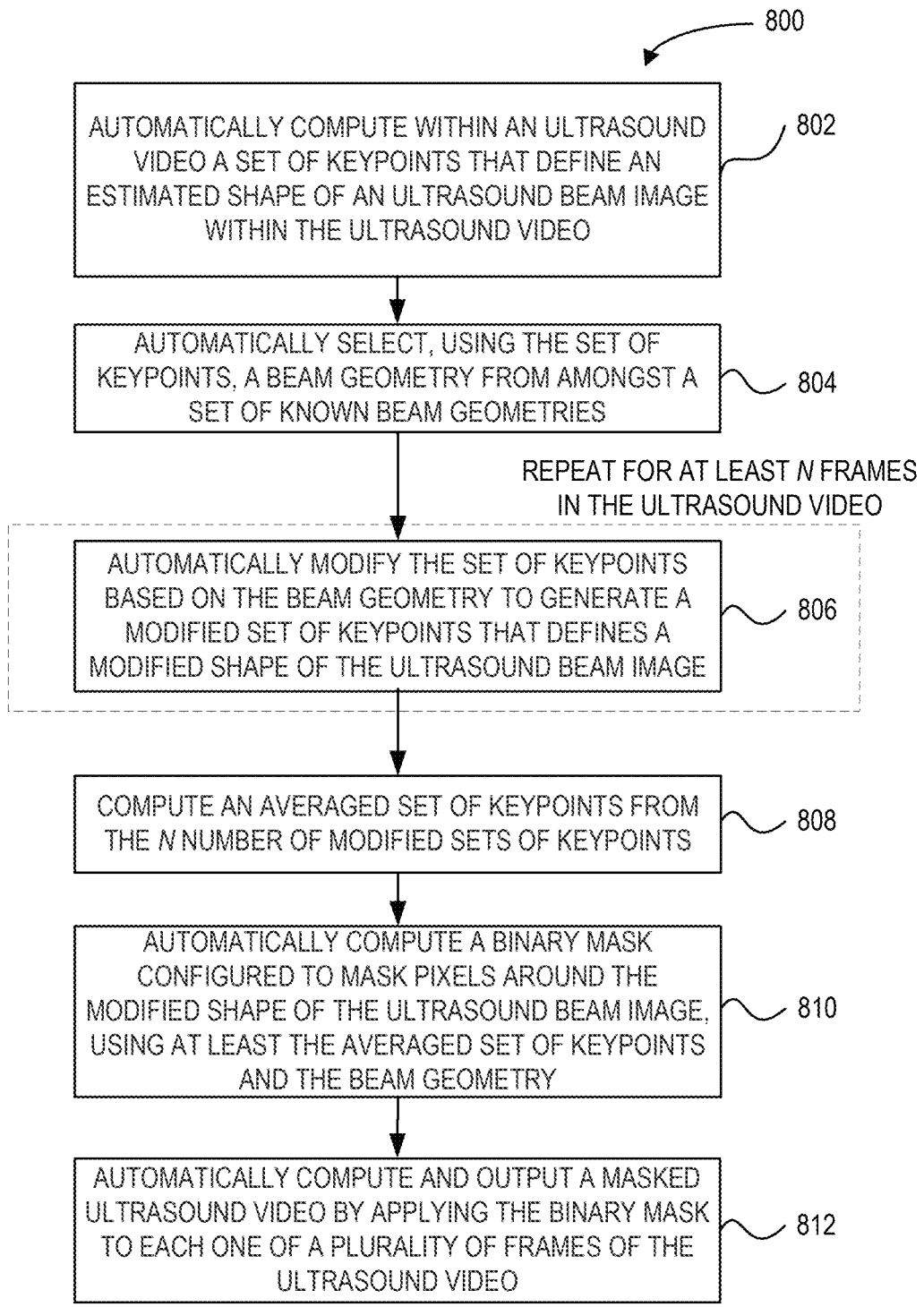
FIG. 8 is a flowchart diagram of an example method of computing a masked ultrasound video in accordance with at least some embodiments.

Referring now to FIG. 8, an example computational method 800 is provided for computing a masked ultrasound video.

Block 802: Automatically compute within the ultrasound video a set of keypoints that define an estimated shape of an ultrasound beam image within the ultrasound video.

Block 804: Automatically select, using the set of keypoints, a beam geometry from amongst a set of known beam geometries.

Block 806: Automatically modify the set of keypoints based on the beam geometry to generate a modified set of keypoints that defines a modified shape of the ultrasound beam image. In some cases, the operation of block 806 is repeated for at least N frames from the ultrasound video.

Block 808: Compute an averaged set of keypoints from the N number of modified sets of keypoints.

Block 810: Automatically compute a binary mask around the modified shape of the ultrasound beam image using at least the modified set of keypoints and the beam geometry.

Block 812: Automatically compute and output a masked ultrasound video by applying the binary mask to each one of a plurality frames of the ultrasound video.

In some cases, the ultrasound image masking process is expressed using the below computations.

inputs: $U \in R^{n \times h \times w \times c}$
$f_\theta : R^{n \times h \times w \times c} \to [0, 1]^7$
// In some cases, the ultrasound video U includes n c-channel images of size h × w
// In some cases, the masking convolutional neural network (CNN) $f_\theta$ has the parameter θ
1. Keypoint Localization
// Predict keypoints p1, p2, p3, p4, where $p_i = (x_i, y_i) \in [0, 1]^2$
$P \leftarrow f_\theta(U)$
// Keypoint localization predictions for all images, $P \in R^{n \times 7}$.

$$(x_1, x_2, x_3, x_4, y_2, y_4) \leftarrow \frac{1}{n}\sum_{i=1}^{n} P_i$$

// Take the mean prediction across all images.
$y_1 \leftarrow y_2$
$y_3 \leftarrow y_4$ // In some alternative cases, $(x_1, x_2, x_3, x_4, y_1, y_3) \leftarrow \frac{1}{n}\sum_{i=1}^{n} P_i$, and compute $y_2 \leftarrow y_1$ and $y_4 \leftarrow y_3$
// In cases where p5 is used to define the bottom boundary, then predict $y_5$ and compute $x_5$.
$x_5 \leftarrow \frac{1}{4}(x_1 + x_2 + x_3 + x_4)$

```
2. Probe Type Prediction
// Predict probe type
probe_type ← predict_probe_type(p1, p2, p3, p4, I)
3. Keypoint Refinement
// Adjust keypoints based on probe type.
if probe_type == "phased array" and |x_2 − x_1| < t_point then
    x_3 ← x_3 + w × s_H
    x_4 ← x_4 − w × s_H
    y_1 ← y_1 + h × s_V
    y_2 ← y_2 + h × s_V
else if probe_type == "linear array" then
    x_1, x_3 ← max(x_1, x_3)       // Ensure rectangular mask
    x_2, x_4 ← max(x_2, x_4)
    y_1, y_2 ← max(y_1, y_2)
    y_3, y_4 ← max(y_3, y_4) // In cases where p5 is used, then y_5 ← min(y_3, y_4)
end if
4. Mask Application
// Compute binary beam mask M based on probe type.
if probe_type == "linear array" then
    M ← 1_[(x≥x1)∧(x≤x3)∧(y≥y1)∧(y≤y3)]
else
    b_1, c_1 ← solve_polynomial (x_1, y_1, x_3, y_3)
    // This solves for the polynomial defining the line connecting p1 and p3.
    b_2, c_2 ← solve_polynomial(x_2, y_2, x_4, y_4)
    // This solves for the polynomical defining the line connecting p2 and p4.
    x_im, y_im ← point_of_intersection (b_1, c_1, b_2, c_2)
    // This is the point of intersection for the left and the right boundary lines
    r_bot ← √((x_im−x_3)^2+(y_im−y_3)^2)
    // This is the radius of the bottom circular boundary (e.g., lower circle arc)
    if probe_type == "phased array" then
        M ← 1
            [(y ≥ y_1) ∧ (y ≥ b_1x + c_1) ∧ (y ≥ b_2x + c_2) ∧ (y ≤ y_im + √(r_bot^2−(x_im−x)^2))]
    else
        r_top ← √((x_im−x_1)^2+(y_im−y_1)^2)
        // This is the radius of the top circular boundary (e.g., upper circle arc) in
        curved linear beam geometries
        M ← 1
            [(y ≤ y_im + √(r_top^2−(x_im−x)^2)) ∧ (y ≥ b_1x + c1) ∧ (y ≥ b_2x + c_2) ∧ (y ≤ y_im +
            √(r_bot^2−(x_im−x)^2))]
    end if
    // In cases where p5 is used to compute a parabola connecting p3, p4 and p5, then
    use the following computation.
    // a_3, b_3, c_3 ← solve_polynomial(x_3, y_3, x_4, y_4, x_5, y_5)
    // M ← 1[(y ≥ y_1) ∧ (y ≥ b_1x + c_1) ∧ (y ≥ b_2x + c_2) ∧ (y ≤ a_3x^2 + b_3x + c_3)]
end if
// Apply beam mask to the image
U ← U ⊙ M  // This is a Hadamard product that is applied across all images.
5. Masked Image Refinement
// Perform quality assurance check and crop image to mask bounds.
I ← quality_assurance_check(I, M)
I ← I[y_1:y_im + r_bot, x_3:x_4]
// In the case where p5 is used to compute a parabola, then I ← [y_1:y_5, x_3:x_4]
return I
```

Below is a discussion of some of the computations in further detail. Computing Keypoint Localization The localization of keypoints is computed to define the vertices of the ultrasound beam shape. As noted above, there are a set of keypoints that define the shape of the ultrasound beam, regardless of the probe type: p1, p2, p3, p4 ∈ real numbers. In some cases, a range [0,1] applies to normalized image space and applies to normalized pixel space, and the values of p1, p2, p3, p4 conform to the normalized image space and applies to normalized pixel space. In some other cases, there are more keypoints: p1, p2, p3, p4, p5. In some other cases, there are even more keypoints used to define the shape of the ultrasound beam.

The objective of this step is to determine the x- and y-coordinates of the keypoints. In some cases, a machine learning approach is applied to the problem, treating the keypoints as regression targets for a deep convolutional neural network. Given a sufficiently large training set of ultrasound images from a variety of manufacturers and probe types, in some cases a deep neural network could learn to adequately predict the locations of the named keypoints for a diverse set of ultrasound probes, including those unseen during training.

In some cases, a deep learning approach is better suited for this task than the use of handcrafted computer vision operations because it is difficult to account for logos, shapes, and textures for devices not considered in development. In some cases, the problem is better posed as keypoint localization than semantic segmentation because the model hypothesis space is greatly simplified—semantic segmentation requires both an encoder and a decoder, whereas a keypoint localization architecture can be realized with only an encoder and some fully connected layers. Additionally, in some cases, keypoint localization and subsequent mask construction always produces exactly one beam mask with clearly defined edges that are faithful to the geometry of the ultrasound beam. A segmentation model may identify multiple disconnected regions, produce beam shapes with jagged edges, or tend to produce false negatives predictions in cases where large portions of the beam cover anechoic (black) structures.

In some cases, the architecture of the keypoint localization neural network model is used. Recall that the keypoint localization problem for masking consists of predicting the coordinates of five named keypoints (see, for example, FIGS. 4A, 4B, 4C and 4D). In some cases, the input to the model is a 3-channel image in RGB format, resized to 224×224 pixels. Although ultrasound beams are typically greyscale, the computing system leverages colour information because burnt-in artifacts are frequently coloured, thereby adding to their distinctness compared to the beam. The output of the model are real-valued x- and y-coordinates of the keypoints in normalized image space. In cases that use four keypoints, there are eight such coordinate outputs. In cases that use five keypoints, there are ten such coordinate outputs. Recalling the relationships given by Equations 1 and 2 (and in some cases Equation 3 when p5 is used), the problem is simplified by only requiring the model to output predictions for a subset of coordinate values: $x_1$, $y_1$, $x_2$, $x_3$, $y_3$, $x_4$. There are six predicted or estimated coordinate values. The Equations 1 and 2 are used to obtain values for $y_2$, and $y_4$ respectively when computing the beam mask. In cases where p5 is used, the point $y_5$ is computed using the prediction model, and Equation 3 is used to compute the coordinate $x_5$. In summary, the input to the model is an RGB image $I \in R^{h \times w \times c}$ and the output is a vector $\vec{p} \in R^6$. In some cases, EfficientNetB0 is an architecture designated for the encoder. In some other cases, a convolutional neural network, or a vision transformer, or variants thereof, could be used as the encoder. In some cases, global average pooling is applied to the feature map outputted by the encoder, followed by dropout, a multi-node fully connected layer with rectified linear unit activation, and finally a multi-node fully connected layer that provides the output of the model. In some other cases, feature map flattening, instead of global average pooling, is applied to the feature map outputted by the encoder.

In some cases, to train the keypoint localization model, a dataset was amassed that includes B-mode lung ultrasound videos from a variety of manufacturers and probe types, collected at an assortment of depths. The dataset was split by video into a training set, validation set, and test set. All images from each video in the training set were used to train the localization model. Video-wise labels were produced for the coordinates of each keypoint. Note that the label for one video applies to all of its constituent images. Keypoint labels were transformed to normalized image space by dividing the x- and y-coordinates of the keypoints by the video's width and height respectively. In normalized image space, (0, 0) corresponds to the top left corner and (1, 1) corresponds to the bottom right corner. Occasionally, some portions of the ultrasound beam were not contained within the bounds of the video. In the labelling regime used in the example cases described herein, these situations corresponded to coordinates outside the range [0, 1]. As a result, the output range of the neural network model was not constrained.

In some cases, the keypoint localization model was permitted to train for a maximum of 50 epochs. In some cases, mean absolute error was designated as the loss function. In some other cases, other types of regression loss functions could be utilized for this problem, such as mean squared error loss and Huber loss. In some cases, the model was optimized using the Adam method, with an initial learning rate of $1 \times 10^{-4}$. In some cases, when the loss on the validation set did not decrease for 3 consecutive epochs, the learning rate was halved. Early stopping was applied to cease training if the loss on the validation set did not decrease after 6 consecutive epochs. In some cases, the model trained for 21 epochs, and the weights of the model corresponding to the lowest validation loss were retained.

In some cases, to increase the diversity of the dataset, stochastic data augmentations were applied during training. At each learning step, a series of random transformations were applied to each training image. In addition to using customary geometric, colourization, and noise transformations, two different computations are executed (also herein called) transformations specifically for the ultrasound beam keypoint localization problem. Each is described below.

Artifact inpainting transformation: This operation is characterized by the insertion of miscellaneous graphics, text, and shapes at random locations external to the ultrasound beam. Specifically, the artifacts are inserted in locations outside a bounding box enclosing the beam, which is determined using keypoint labels. In some other cases, alternative versions of this augmentation place graphical entities at all locations of the image. The locations of the entities could be sampled from a probability density function over the coordinates that favour locations external to the beam.

Figure 9:
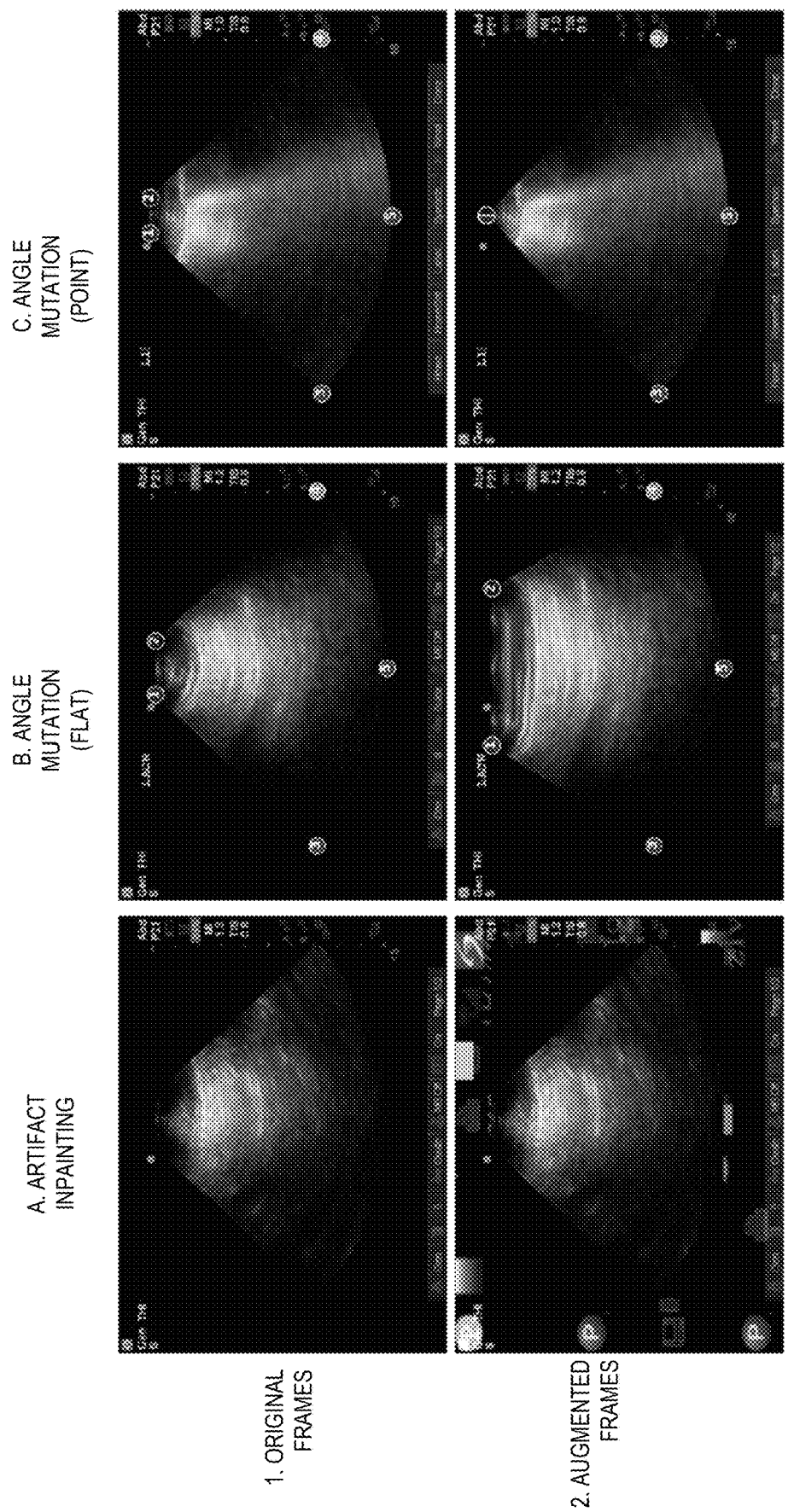
FIG. 9 is a chart of example ultrasound images representing artifact inpainting and angle mutation augmentations used to train a keypoint localization model.

In some cases, the graphics are randomly selected from a predefined set of image files that contains logos and icons sourced from various ultrasound videos. The inpainted text artifacts are randomly generated strings with random font, size, and colour. Similarly, the type, colour, and size of inpainted shapes are random. The intent of this augmentation is to improve the model's invariance to a wide set of possible artifacts that it may encounter when presented with images containing artifacts different than those in the training set. FIG. 9 (column A) illustrates the effect of this transformation.

Angle mutation transformation: Inspired by the diversity of beam shapes in phased array and curved linear videos, this transformation modifies beams of these types by simulating a widened or narrowed angle between the left and right lateral bounds of the beam. Given the input stretching factor $\phi \in R^+$, the angle mutation transformation applies a nonlinear warp to the image to produce a distorted version of it where p1 and p2 are horizontally separated by $\phi \cdot |x_2 - x_1|$, while p3, p4, and p5 remain unchanged. The nonlinear warp is applied using a dense flow field computed for each pixel in the image. Note that $\phi > 1$ corresponds to horizontally stretching the top of the beam, while $\phi < 1$ results in horizontal compression. In the special case where $\phi = 0$, the image is transformed to produce a phased array (point) beam shape. In some cases, the computing system applies this transformation with probability 0.33. When the transformation is applied, $\phi$ is set to 0 with probability 0.5. Otherwise, in some other cases, $\phi$ is drawn from a uniform distribution over $$\left[0, \min\left(3, \frac{x_4 - x_2}{x_2 - x_1} - 1\right)\right]. \text{ The } \frac{x_4 - x_2}{x_2 - x_1} - 1$$

factor ensures that the augmentation does not transform the keypoints outside of the bounds of p3 and p4. See FIG. 9 for visual demonstrations of the angle mutation transformation when $\phi > 1$ (column B) and $\phi = 0$ (column C).

In some cases, the following sequence of stochastic data augmentation transformations were applied to each phased array and curved linear training image. Unless a probability of application is specified, all transformations were applied with probability 1.

1. Angle mutation transformation (with probability 0.33)
2. Artifact inpainting transformation (with probability 0.5)
3. Zoom in or out by $z_x$ in the horizontal dimension and zoom out by $z_y$ in the vertical dimension, where $z_x \sim U(-0.5, 0.5)$ and $z_y \sim (0, 0.5)$
4. Translation in the horizontal direction by $t_x \in U(-0.1, 0.1)$ and in the vertical direction by $t_y \in U(-0.1, 0.1)$
5. Random horizontal flip (with probability 0.5)
6. Contrast adjustment by $c \sim U(0.8, 1.2)$
7. Multiplicative noise, where each pixel is multiplied by a value $m \sim U(0.8, 1.2)$ In some cases, linear clips were subjected to the same set of transformations, with the exception of the angle mutation transformation. Keypoint labels were modified after each geometric transformation to ensure that they aligned with the appropriate coordinates in transformed image space.

The model was quantitatively evaluated by assessing its performance on the test set. Table 1 provides example performance metrics for the final model on the training, validation, and test set. Across all the images in the test set, it achieved a mean absolute error of $2.8 \times 10^{-3}$. Performance on the validation and test sets was better than on the training set, underlining the heightened difficulty of the examples introduced by the data augmentation transformations. The average absolute error in keypoint coordinate prediction was 0.28% of the height or width of the image, which amounts to less than one pixel for 224×224 images. The performance of the keypoint localization model was deemed acceptable.

TABLE 1

Training, validation, and test set metrics for the keypoint localization model.

| Metric | Training Set | Validation Set | Test Set |
| --- | --- | --- | --- |
| Mean absolute error | $6.3 \times 10^{-3}$ | $2.5 \times 10^{-3}$ | $2.8 \times 10^{-3}$ |
| Mean squared error | $8.9 \times 10^{-5}$ | $2.6 \times 10^{-5}$ | $3.5 \times 10^{-5}$ |
| Root mean squared error | $9.4 \times 10^{-3}$ | $5.1 \times 10^{-3}$ | $5.9 \times 10^{-3}$ |

It will be appreciated that different keypoint localization models could have different training, validation and test set metrics other than the example shown in Table 1.

In some cases, the keypoint localization step of the masking method is characterized by executing the forward pass of the trained keypoint localization model. The forward pass is invoked for each image in the video. Most modern deep learning frameworks support batched inference, facilitating efficient invocation for several images comprising a single video. The output of the forward pass applied to an n-image video is a matrix $P \in R^{n \times 7}$ containing the predicted coordinates for each image. A single set of coordinates that describes the mask for the entire video is obtained by taking the average value for each predicted coordinate across all n images. As described above, Equations 1 and 2 (and in some cases Equation 3 as well) are applied to set the values of the remaining coordinates. The resulting tuple of predicted keypoints (p1, p2, p3, p4) is then passed to the probe type prediction step. In the case where p5 is used, then the predicted keypoints include p1, p2, p3, p4 and p5.

Probe Type Prediction

It is recognized by the inventors of this patent application that, in some cases, by adopting a keypoint localization approach, a sufficiently close prediction contains the necessary information required to determine the type of the probe. Recall that the type of probe dictates the form of the beam. As will be detailed in the below section Keypoint Refinement, knowledge of the probe type is useful for improving the positions of the keypoints predicted by the localization model. See FIGS. 10A, 10B, and 10C for a helpful visual accompaniment to the predict_probe_type( ) computation description below.

The probe type prediction computation receives the input image and the set of predicted keypoints as input. The relative positions of the predicted keypoints are then used to estimate whether the probe is phased array, curved linear array, or linear array. If the absolute difference between $x_1$ and $x_3$ are within a small threshold $t_{linear}$ of each other, then the leftmost line is likely vertical. If $x_2$ and $x_4$ also satisfy this condition, then the rightmost line is likely vertical. In some cases, the distance is measured in units suitable for image pixel coordinate space or for normalized image coordinate space. Other units of distance can be used to correspond to image processing.

Accordingly, if both of these conditions are satisfied, the probe type is predicted to be linear. Otherwise, a check is performed for the phased array (point) case. If the absolute difference between $x_1$ and $x_2$ is within a small threshold $t_{phased}$, then the probe is predicted to be phased array. If none of the above conditions are met, there are two options remaining: either the clip is curved linear array, or it is a case of a phased array probe where the top of the beam is a horizontal line. To distinguish between these two cases, a square region of interest (ROI) is defined that is horizontally centered between $x_1$ and $x_2$ and vertically positioned such that its top edge is colinear with a horizontal straight line drawn between p1 and p2 (by design, $y_1 = y_2$). In some other cases, the masking computation utilizes a curved region of interest based on the arc of a circle computed using the point of intersection of the lateral linear bounds.

In some cases, the length of each edge of the region of interest is $R \cdot |x_2 - x_1|$, where $R \in (0, 1)$ is a constant. For a curved linear clip, the ROI should largely be black, as it would be outside of the US beam. For a phased array clip with a horizontal top bound, the ROI would, with high probability, contain mostly non-black pixels that are contained within the beam. As such, if the average pixel intensity of each pixel in the ROI is below a threshold $t_{curved}$, then the probe is predicted to be curved linear array; otherwise, it is predicted to be phased array.

Below is a computation for predict_probe_type( ) which is used in the ultrasound masking process, according to at least some embodiments.

inputs: p1, p2, p3, p4, p5, where $pi = (x_i, y_i) \in [0, 1]^2$
// These keypoints are in normalized image space.
    $I \in R^{h \times w \times c}$   // This is the ultrasound image.
    $t_{linear}, t_{curved}$,   // These are thresholds for each probe type.
    $t_{phased}$
    R   // This is the width of the top centre ROI in curved linear probes.
if $|x_3 - x_1| < t_{linear}$ and $|x_4 - x_2| < t_{linear}$ then
  return "linear"   // The left and right bounds are vertical lines.
else if $|x_2 - x_1| < t_{phased}$ then
  return "phased_array"
  // The tops of the left and right bounds meet at a point.
end if $x_m \leftarrow \frac{1}{2}(x_2 - x_1)$   // This is the midpoint between top keypoints.

$r \leftarrow R |x_2 - x_1|$   // This is the width of square ROI.

$$ROI \leftarrow I\left[\max(0, y_1) : \min(y_1 + r, w), \max\left(x_m - \frac{r}{2}, 0\right) : \min\left(x_m + \frac{r}{2}, h\right.\right.$$

```
if E[ROI] < t_curved then
    return "curved_linear"
    //This is the average pixel intensity in the ROI is below a threshold.
else
    return "phased_array"
end if
```

Figure 10A:
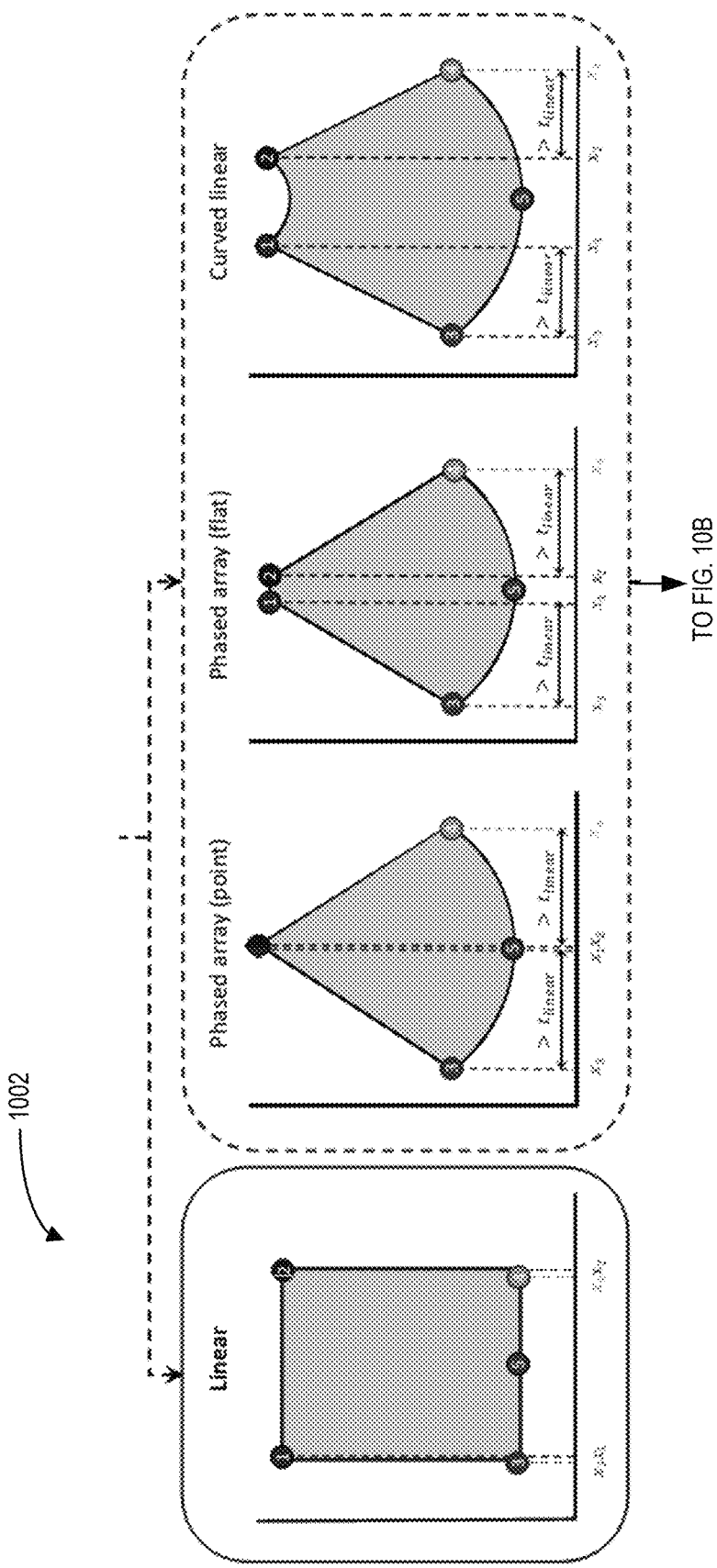
FIGS. 10A, 10B, and 10C is a schematic representation of the methods used to predict a probe type.
Figure 10B:
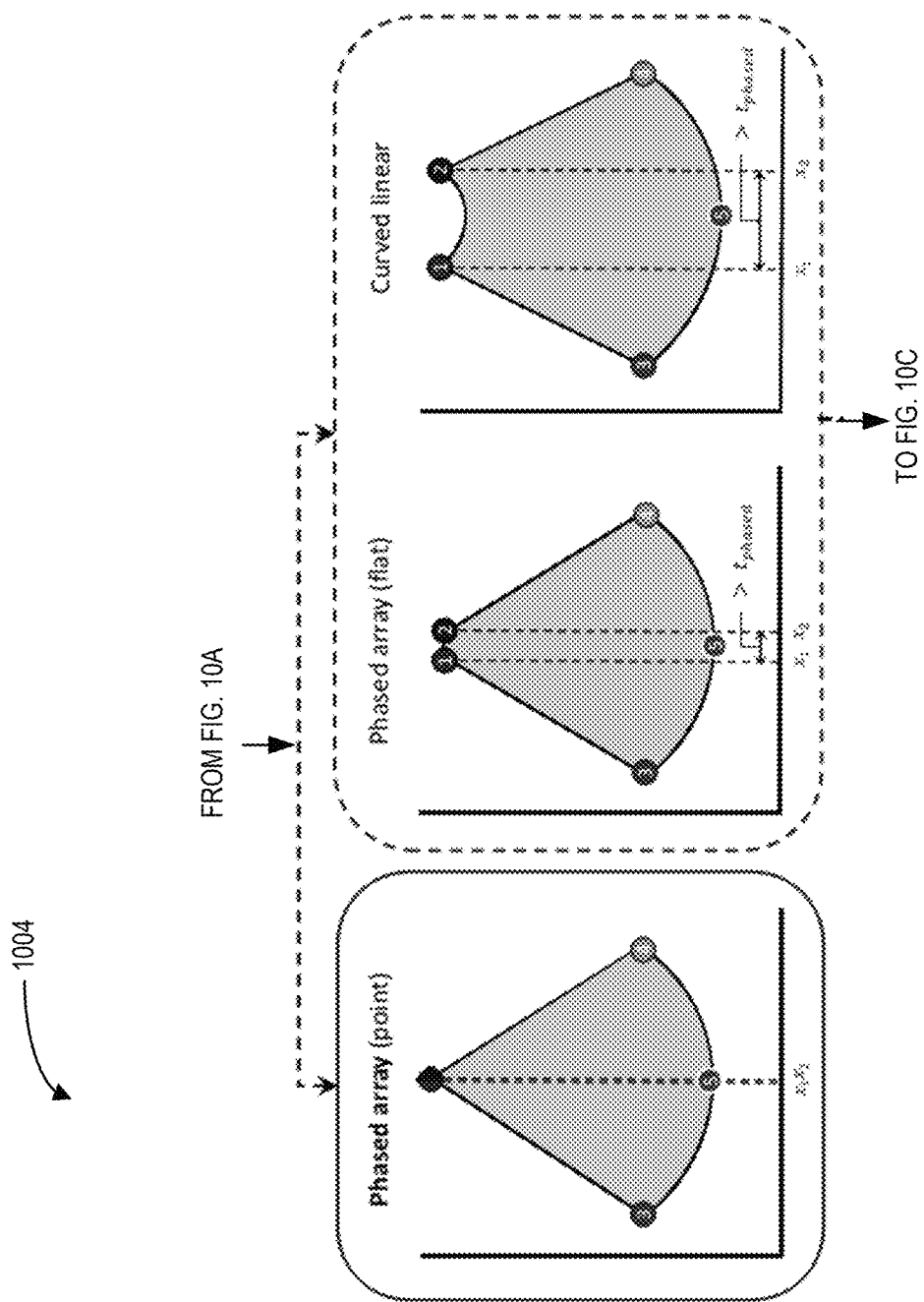
Figure 10C:
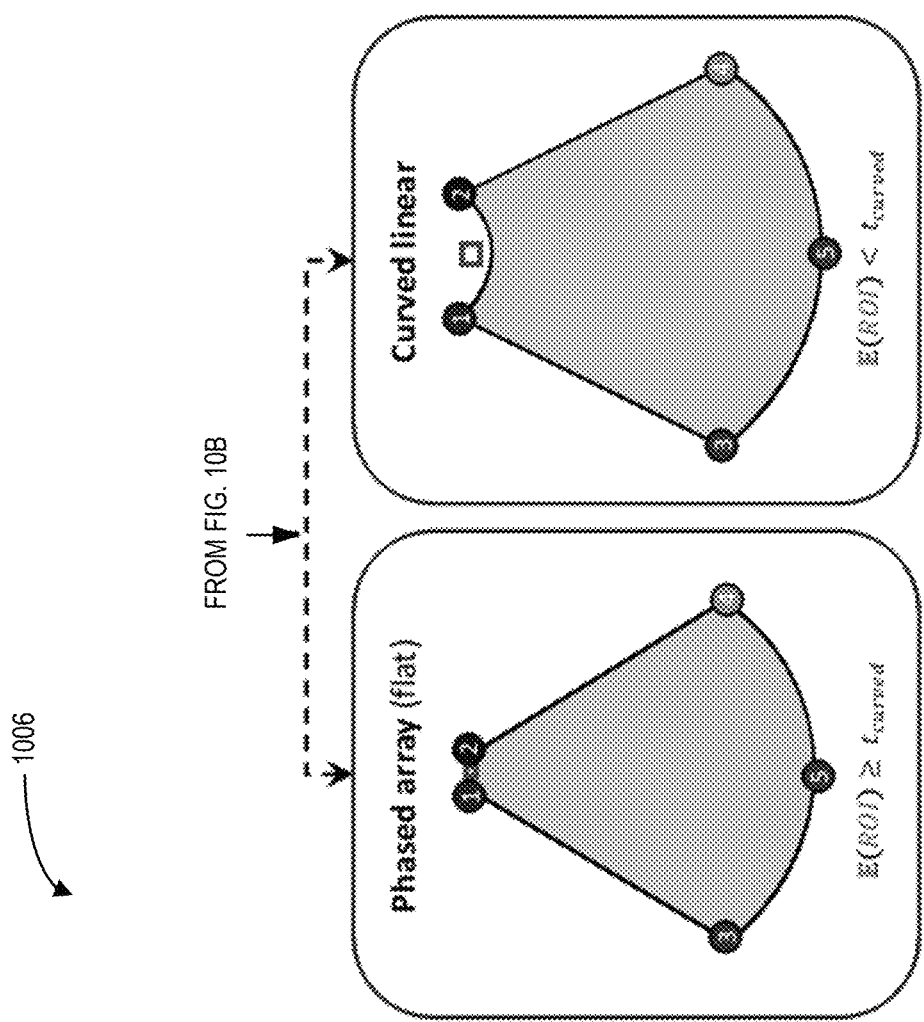

As shown in FIGS. 10A, 10B, 10C, schematic representations of the methods used by predict_probe_type( ) Given a list of keypoints, the following probe types are predicted: linear, phased array, and curved linear. Beginning with 1002: If the edges of the ultrasound beam are approximately vertical (i.e. $|x_3-x_1|<t_{linear}$ and $|x_4-x_2|<t_{linear}$), then return linear. If not, the computing system proceeds to 1004: If p1 and p2 are adjacent (i.e. $|x_2-x_1|<t_{phased}$), then return the phased array. If not, the computing system proceeds to 1006: Define a small region of interest (ROI) underneath the horizontal midpoint of p1 and p2. If the ROI encloses the mask, or in other words, if the pixels in the ROI are black (i.e. $E(ROI)<t_{curved}$), then return curved linear. Otherwise, the computing system returns the phased array.

Keypoint Refinement

Acknowledging that machine learning models for keypoint localization are imperfect, the computing system leverages the probe type prediction to make refinements to the predicted keypoints. Tailored to the probe type, in some cases, the refinements modify the keypoints to improve the predicted shape of the ultrasound beam such that it adheres to the geometrical description of the beam shapes described above. In some cases, such modifications result in the exclusion of a small number of pixels on the periphery of the beam. To reduce the chances of including any pixels that do not lie within the actual ultrasound beam, the computations err on the side of caution in these cases by moving keypoints toward the centre of the beam instead of away from it. Since some ultrasound videos contain artifacts that meet the boundary of the beam, it is considered to be less harmful to erroneously remove a few pixels on the periphery of the beam than it would be to retain such artifacts after masking.

For phased array (point) clips, the computing system horizontally translate $x_3$ and $x_4$ toward the beam centre by a fraction $s_H$ of the image width, where $s_H \in R^+$ is a small positive constant. In some cases, the masking algorithm explicitly sets $$x_1, x_2 \leftarrow \frac{1}{2}(x_1 + x_2)$$

for phased array (point) clips.

Additionally, the computing system translates $y_1$ and $y_2$ downwards by a fraction $s_V$ of the image height, where $s_V \in R^+$ is another small positive constant. The above refinements are motivated by manual investigation of the keypoint localization model's predictions for phased array (point) images. It is observed that, in these cases, the model would predict keypoints that were just outside the beam's bounds. By slightly moving select coordinates toward the centre of the beam as described above, masks for phased array (point) are less likely to contain slivers of pixels located directly lateral to the beam. In some cases, the keypoint localization model's is prone to making approximate errors for phased array (point) because the phased array (point) is a sharp mode in the distribution of phased array shapes, as the width of the top bound in other phased array examples is more broadly distributed.

When the probe type is predicted to be linear, the computing system enforces that the resulting ultrasound beam mask is rectangular in shape. In some cases, out of caution in defining the bounds of the beam, the computing system remove pixels on the periphery of the beam instead of including any extraneous pixels. Therefore, the left, right, top, and bottom bounds of the beam are defined to be $\max(x_1, x_3)$, $\min(x_2, x_4)$, $\max(y_1, y_2)$, and $\min(y_3, y_4)$ respectively. The keypoint predictions are then updated so that they lie on the edges of the resultant rectangle.

Mask Application

At this stage, the mask M is constructed and applied to each image in the ultrasound video. The shape of the mask depends on the predicted probe type. Recall that the mask is a binary matrix $M \in \{0, 1\}^{h \times w}$ that indicates which pixels in a h×w image are to be retained. Using the refined keypoints, equations defining the bounds of the mask are determined. In some cases, all points lying within the closed region formed by the intersections of these bounds constitute the ultrasound beam and are thus set to 1 in the mask. All other points are set to 0, as they correspond to regions external to the ultrasound beam.

When the predicted probe type is linear, the bounds of the mask correspond to straight lines. The left bound is $x=x_1$, the top bound is $y=y_1$, the right bound is $x=x_3$, and the bottom bound is $y=y_3$. All points situated within these bounds correspond to the rectangular-shaped ultrasound beam.

If the probe type is not linear, the computing system constructs a region with the general form of a phased array beam. In some cases, curved linear array are top bound by a circular arc (e.g., a portion of a circumference of a circle) that extends from p1 to p2. In some other cases, the top bound is the horizontal line $y=y_1$. Note that this top bound applies generally to phased array clips and defines the top bound of curved linear array (also called curved linear clips). The left and right lateral bounds are slanted lines with negative and positive slopes respectively. Given p1 and p3, the computing system solves for the coefficients of the equation of the line describing the left bound: $y=b_1x+c_1$. Similarly, p2 and p4 are used to solve for the equation of the right bound: $y=b_2x+c_2$. In some cases, the bottom bound of phased array and curved linear clips will be a circular arc extending from p3 to p4. A circle's equation can be derived if its radius and the location of its centre are known. The centre is the point of intersection of the left and right bounds, and the radius is the Euclidean distance from its center to p3.

In some other cases in which a parabola is used to define the curved bottom boundary, the computing system solves for the equation of a quadratic polynomial constituting the rounded bottom bound of the beam. Using points p3, p4, and p5 as three known points on the parabola, the computing system solves for its equation: $y=a_3x^2+b_3x+c_3$.

All points that lie below the equations for the top and lateral bounds and that lie above the bottom bound correspond to the ultrasound beam.

After the binary mask has been determined, it is applied to each image in the video to set all pixels outside the ultrasound beam to 0. To perform the masking operation, the computing system computes the Hadamard product of the binary mask and each image in the video. The resulting products constitute the images of the masked video.

Masked Image Refinement

After the application of the initial mask obtained from previous steps, the masked image is refined to address any leftover artifacts, typically found inside the bounds of the ultrasound beam. In some cases, the first step is the application of Optical Character Recognition (OCR) to detect any leftover text on the image. Then, a check for non-text artifacts is performed. This process is built on the assumption that pixels displaying ultrasound data will have higher pixel intensity variation across frames compared to static artifacts. Therefore, we first compute the pixel-wise coefficient of variation (CV) across frames, using the standard deviation of each pixel's intensity across frames, $\sigma$, and the mean pixel intensity of the clip, $\mu$:

$$CV = \sigma/\mu$$

Any pixel with a CV above a CV threshold, $t_{CV}$, is characterized as containing useful ultrasound data. For a given ultrasound frame, we then remove all pixels containing useful ultrasound data, leaving only pixels belonging to the background or leftover artifacts. Simple contour detection is then applied along the edges of the resulting image to localize leftover edge artifacts. Finally, the surroundings of each leftover artifact contour (including text artifacts from OCR) on the original masked image are checked for nearby ultrasound data pixels. In some cases, if the surrounding pixels can be characterized as background only, i.e. are below the CV threshold $t_{CV}$, then the artifact pixels are set to black. If the surroundings contain pixels that were characterized as containing useful ultrasound data, i.e. are above the CV threshold $t_{CV}$, then the clip is discarded.

If a clip passes this quality assurance check, then each constituent frame is cropped to maximize the information it contains. Indeed, when training deep neural networks for computer vision tasks, images are customarily downsized to a fixed dimension. Since a substantial portion of a correctly masked clip consists of black regions exterior to the ultrasound beam, the ultrasound beam is excessively downsampled. To preserve as much relevant information within the ultrasound beam itself as possible, all masked frames are cropped to the smallest rectangle that entirely contains the beam. The top, left, bottom, and right bounds of the crop are $y_1$, $x_3$, $y_3$, and $x_4$, respectively. The cropping operation marks the end of the masking process.

Evaluation: Generalization to Unseen Vendors

To assess the generalizability of the masking method on unseen vendors, an open-source COVIDx-US (e.g., ultrasound) dataset for ultrasound image analysis was used. The dataset contains ultrasound clips from a diverse set of data sources and vendors, including, but not limited to: the POCUS Atlas, Butterfly Network, Clarius, Hitachi, and HP ultrasound machines.

Figure 11:
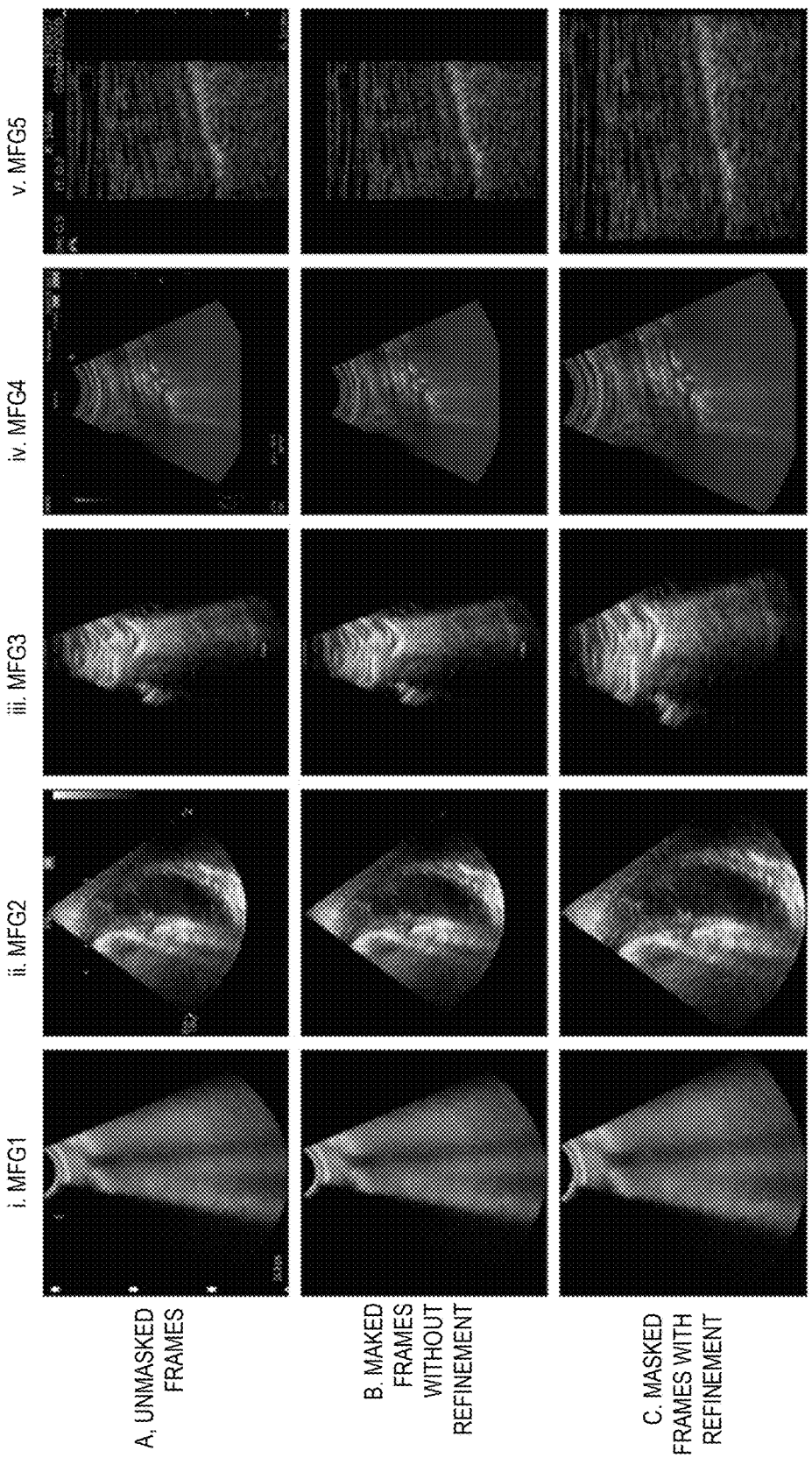
FIG. 11 is a series of example ultrasound images showing that the masking method can be generalized to unseen various ultrasound manufacturers, in accordance with at least some embodiments.

FIG. 11 presents a qualitative analysis of the masking method's performance on a set of exemplar clips from these manufacturers and data sources. Unmasked images (row A) are compared to both unrefined (row B) and refined (row C) masked images. Refinement includes both keypoint (step 3) and masked image refinement (step 5). The masking method performs well on clips acquired from ultrasound machine vendors not present in the original training set (Clarius (column i), HP (column ii), Butterfly Network (column iii), and Hitachi ultrasound machines (column iv)). This is true irrespective of probe type or beam geometry, with the method also successfully masking several cases where the bottom or sides of the beam are cropped off (column iv). The keypoint and masked image refinement steps were essential in removing any artifacts adjacent to (panel A.ii; tick marks) and overlapping the beam (panel B.iii; text at the top (white) and bottom (green) of the beam).

COVIDx-US was originally cleaned for public use via manual identification and individual removal of beam artifacts. Each time a new clip was added to the dataset, the location of its artifacts had to be manually identified and added to a clip-specific dictionary. A proficient and generalizable approach to masking such as that proposed above eliminates this bottleneck in scalability.

Various systems or processes have been described to provide examples of embodiments of the claimed subject matter. No such example embodiment described limits any claim and any claim may cover processes or systems that differ from those described. The claims are not limited to systems or processes having all the features of any one system or process described above or to features common to multiple or all the systems or processes described above. It is possible that a system or process described above is not an embodiment of any exclusive right granted by issuance of this patent application. Any subject matter described above and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

For simplicity and clarity of illustration, reference numerals may be repeated among the figures to indicate corresponding or analogous elements. In addition, numerous specific details are set forth to provide a thorough understanding of the subject matter described herein. However, it will be understood by those of ordinary skill in the art that the subject matter described herein may be practiced without these specific details. In other instances, well-known methods, procedures, and components have not been described in detail so as not to obscure the subject matter described herein.

The terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices are directly connected to one another or connected to one another through one or more intermediate elements or devices via an electrical element, electrical signal, or a mechanical element depending on the particular context. Furthermore, the term "operatively coupled" may be used to indicate that an element or device can electrically, optically, or wirelessly send data to another element or device as well as receive data from another element or device.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

Terms of degree such as "substantially", "about", and "approximately" as used herein mean a reasonable amount of deviation of the modified term such that the result is not significantly changed. These terms of degree may also be construed as including a deviation of the modified term if this deviation would not negate the meaning of the term it modifies.

Any recitation of numerical ranges by endpoints herein includes all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the result is not significantly changed.

Some elements herein may be identified by a part number, which is composed of a base number followed by an alphabetical or subscript-numerical suffix (e.g. 112*a*, or 112*b*). All elements with a common base number may be referred to collectively or generically using the base number without a suffix (e.g., 112).

The systems and methods described herein may be implemented as a combination of hardware or software. In some cases, the systems and methods described herein may be implemented, at least in part, by using one or more computer programs, executing on one or more programmable devices including at least one processing element, and a data storage element (including volatile and non-volatile memory and/or storage elements). These systems may also have at least one input device (e.g. a pushbutton keyboard, mouse, a touchscreen, and the like), and at least one output device (e.g. a display screen, a printer, a wireless radio, and the like) depending on the nature of the device. Further, in some examples, one or more of the systems and methods described herein may be implemented in or as part of a distributed or cloud-based computing system having multiple computing components distributed across a computing network. For example, the distributed or cloud-based computing system may correspond to a private distributed or cloud-based computing cluster that is associated with an organization. Additionally, or alternatively, the distributed or cloud-based computing system be a publicly accessible, distributed or cloud-based computing cluster, such as a computing cluster maintained by Microsoft Azure™, Amazon Web Services™, Google Cloud™, or another third-party provider. In some instances, the distributed computing components of the distributed or cloud-based computing system may be configured to implement one or more parallelized, fault-tolerant distributed computing and analytical processes, such as processes provisioned by an Apache Spark™ distributed, cluster-computing framework or a Databricks™ analytical platform. Further, and in addition to the CPUs described herein, the distributed computing components may also include one or more graphics processing units (GPUs) capable of processing thousands of operations (e.g., vector operations) in a single clock cycle, and additionally, or alternatively, one or more tensor processing units (TPUs) capable of processing hundreds of thousands of operations (e.g., matrix operations) in a single clock cycle.

Some elements that are used to implement at least part of the systems, methods, and devices described herein may be implemented via software that is written in a high-level procedural language such as object-oriented programming language. Accordingly, the program code may be written in any suitable programming language such as Python or Java, for example. Alternatively, or in addition thereto, some of these elements implemented via software may be written in assembly language, machine language or firmware as needed. In either case, the language may be a compiled or interpreted language.

At least some of these software programs may be stored on a storage media (e.g., a computer readable medium such as, but not limited to, read-only memory, magnetic disk, optical disc) or a device that is readable by a general or special purpose programmable device. The software program code, when read by the programmable device, configures the programmable device to operate in a new, specific, and predefined manner to perform at least one of the methods described herein.

Furthermore, at least some of the programs associated with the systems and methods described herein may be capable of being distributed in a computer program product including a computer readable medium that bears computer usable instructions for one or more processors. The medium may be provided in various forms, including non-transitory forms such as, but not limited to, one or more diskettes, compact disks, tapes, chips, and magnetic and electronic storage. Alternatively, the medium may be transitory in nature such as, but not limited to, wire-line transmissions, satellite transmissions, internet transmissions (e.g., downloads), media, digital and analog signals, and the like. The computer usable instructions may also be in various formats, including compiled and non-compiled code.

While the above description provides examples of one or more processes or systems, it will be appreciated that other processes or systems may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be revisited.

What is claimed is:

1. A system for masking an ultrasound image, comprising:
a memory storing instructions; and
a processor coupled to the memory, the processor being configured to execute the instructions to:
    automatically compute within the ultrasound image a set of keypoints that define an estimated shape of an ultrasound beam image within the ultrasound image;
    automatically select, using the set of keypoints, a beam geometry from amongst a set of known beam geometries;
    automatically modify the set of keypoints based on the beam geometry to generate a modified set of keypoints that defines a modified shape of the ultrasound beam image;
    automatically compute a binary mask configured to mask pixels around the modified shape of the ultrasound beam image, using at least the modified set of keypoints and the beam geometry; and
    automatically compute and output a masked ultrasound image using at least the binary mask.

2. The system of claim 1, wherein the set of keypoints comprises points p1, p2, p3, and p4, wherein p1 refers to a coordinate $(x_1,y_1)$ at a top left corner of the estimated shape of the ultrasound beam image; p2 refers to a coordinate $(x_2,y_2)$ at a top right corner of the estimated shape of the ultrasound beam image; p3 refers to a coordinate $(x_3,y_3)$ at a bottom left corner of the estimated shape of the ultrasound beam image; p4 refers to a coordinate $(x_4,y_4)$ at a bottom right corner of the estimated shape of the ultrasound beam image.

3. The system of claim 2, wherein the set of keypoints further comprises point p5, which refers to a coordinate $(x_5,y_5)$ at a bottom centre of the estimated shape of the ultrasound beam image.

4. The system of claim 1, wherein the processor is configured to execute the instructions to automatically compute within the ultrasound image the set of keypoints by at least:
  inputting the ultrasound image into a prediction model that predicts at least a subset of values of the set of keypoints;
  wherein additional values of the set of keypoints are computed based on known relationships between the additional values of the set of keypoints and one or more of the subset of values of the set of keypoints; and
  wherein the prediction model is a neural network model.

5. The system of claim 4, wherein the neural network model is a deep convolutional neural network and the set of keypoints are a set of regression targets for the deep convolutional neural network.

6. The system of claim 4, wherein the neural network model is a vision transformer or a variant of the vision transformer and the set of keypoints are a set of regression targets for the vision transformer.

7. The system of claim 2, wherein the processor is configured to execute the instructions to automatically compute within the ultrasound image the set of keypoints by at least inputting the ultrasound image into a prediction model that predicts at least a subset of values of the set of keypoints, and wherein the subset of values of the set of keypoints comprise: $x_1$, $y_1$, $x_2$, $x_3$, $y_3$, and $x_4$.

8. The system of claim 7, wherein the prediction model is a neural network model configured to predict $x_1$, $y_1$, $x_2$, $x_3$, $y_3$, and $x_4$; and the processor is configured to execute the instructions to automatically compute $y_2$ and $y_4$ using at least:
  Equation 1 comprising $y_1=y_2$; and
  Equation 2 comprising $y_3=y_4$.

9. The system of claim 7, wherein the prediction model is a neural network model configured to predict $x_1$, $y_2$, $x_2$, $x_3$, $y_4$, and $x_4$; and the processor is configured to execute the instructions to automatically compute $y_1$ and $y_3$ using at least:
  Equation 1 comprising $y_2=y$; and
  Equation 2 comprising $y_4=y_3$.

10. The system of claim 1, wherein the set of known beam geometries comprises a phased array point geometry, and wherein the phased array point geometry comprises a region bounded by at least a portion of a circumference of a circle below the region, a left line with a first slope above the portion of the circumference of the circle, a right line with a second slope above the portion of the circumference of the circle, and the left line and the right line intersect at a point above the portion of the circumference of the circle.

11. The system of claim 1, wherein the set of known beam geometries comprises a phased array flat geometry, and wherein the phased array flat geometry comprises a region bounded by at least a portion of a circumference of a circle below the region, a left line with a first slope above the portion of the circumference of the circle, a right line with a second slope above the portion of the circumference of the circle, and the left line and the right line intersect opposite ends of a top line above the portion of the circumference of the circle.

12. The system of claim 1, wherein the set of known beam geometries comprises a curved linear array geometry, wherein the curved linear array geometry comprises a region bounded by at least a first portion of a circumference of a first circle below the region, a left line with a first slope above the first portion of the circumference of the first circle, a right line with a second slope above the first portion of the circumference of the first circle, and the left line and the right line intersect opposite ends of a second portion of a circumference of a second circle; wherein the second portion of the circumference of the second circle is positioned above the first portion of the circumference of the first circle, and the second portion of the circumference of the second circle and the first portion of the circumference of the first circle have a same orientation.

13. The system of claim 1, wherein the set of known beam geometries comprises a linear array geometry, and wherein the linear array geometry comprises a rectangular geometry.

14. The system of claim 3, wherein the set of known beam geometries comprises a phased array point geometry, a phased array flat geometry, a curved linear array geometry, and a linear array geometry; and
  wherein the processor is further configured to compute a first determination that $|x_3-x_1|<t_{linear}$ and $|x_4-x_2|<t_{linear}$, wherein $t_{linear}$ is a threshold distance associated with the linear array geometry, then select the linear array geometry as the beam geometry.

15. The system of claim 14, wherein the processor is configured to, after determining that the first determination is not applicable to the set of keypoints comprising p1, p2, p3, p4 and p5, compute a second determination that $|x_2-x_1|<t_{phased}$, wherein $t_{phased}$ is a threshold distance associated with the phased array point geometry, and then select the phased array point geometry as the beam geometry.

16. The system of claim 15, wherein, when $|x_2-x_1|<t_{phased}$, the processor is configured to automatically set $x_2$ and $x_1$ to equal $(x_1+x_2)/2$, to be consistent with the phased array point geometry.

17. The system of claim 15, wherein the processor is configured to, after determining that the second determination is not applicable to the set of keypoints, compute a third determination by:
  computing a region of interest below a horizontal midpoint of p1 and p2, and determining that a pixel colour value of the region of interest matches a masking pixel colour value;
  then select the curved linear array geometry as the beam geometry.

18. The system of claim 17, wherein the processor is configured to, after determining that the third determination is not applicable to the set of keypoints, select the phased array flat geometry as the beam geometry.

19. The system of claim 2, wherein the processor is configured to execute the instructions to automatically modify the set of keypoints based on the beam geometry to generate the modified set of keypoints that defines the modified shape of the ultrasound beam image by at least: translating at least one of the set of keypoints to generate the modified shape that matches the beam geometry.

20. The system of claim 1, wherein the binary mask is constructed as a Boolean tensor and the binary mask comprises pixels that form an ultrasound image region that corresponds to the modified shape of the ultrasound beam image.

21. The system of claim 1, wherein the processor is configured to execute the instructions to automatically compute the masked ultrasound image using at least the binary mask by at least: computing a Hadamard product of the binary mask and the ultrasound image.

22. The system of claim 1, wherein the processor is configured to execute the instructions to further:
  automatically perform optical character recognition on the masked ultrasound image to detect text; and after detecting the text, set pixels of the text to a pixel color matching the binary mask.

23. The system of claim 1, wherein the ultrasound image is a given frame in an ultrasound video that comprises a plurality of frames; and the plurality of frames of the ultrasound video are automatically inputted into a neural network model to predict the set of key points; and, wherein the processor is configured to execute the instructions to automatically compute a Hadamard product of the binary mask and each one of the plurality of frames of the ultrasound video to generate a plurality of masked frames that form a masked ultrasound video.

24. The system of claim 23, wherein the processor is configured to execute the instructions to further:

compute a pixel coefficient of variation (CV) across the plurality of masked frames using $CV=\sigma/\mu$, wherein $\sigma$ is a standard deviation of each pixel's intensity across the plurality of frames and $\mu$ is a mean pixel intensity of the masked ultrasound video;

identify a set of pixels in the masked ultrasound video as comprising ultrasound data, wherein each pixel in the set of pixels has a CV value above $t_{CV}$, wherein $t_{CV}$ is a CV threshold;

remove the set of pixels from the masked ultrasound video to produce a plurality of modified intermediate frames of the masked ultrasound video;

applying contour detection to one or more edges in each of the modified intermediate frames of the masked ultrasound video to identify one or more pixels as artifacts; and for each one of the plurality of masked frames of the masked ultrasound video, modify the one or more pixels identified as artifacts to have a same color matching the binary mask.

25. A system for masking an ultrasound video, comprising:

a memory storing instructions; and a processor coupled to the memory, the processor being configured to execute the instructions to:

automatically compute within the ultrasound video a set of keypoints that define an estimated shape of an ultrasound beam image within the ultrasound video;

automatically select, using the set of keypoints, a beam geometry from amongst a set of known beam geometries;

repeat a process for each one of a plurality of N frames of the ultrasound video, the process comprising automatically modifying the set of keypoints based on the beam geometry to generate a modified set of keypoints that defines a modified shape of the ultrasound beam image;

compute an averaged set of keypoints from an N number of modified sets of keypoints;

automatically compute a binary mask configured to mask pixels around the modified shape of the ultrasound beam image, using at least the averaged set of keypoints and the beam geometry; and automatically compute and output a masked ultrasound video by applying the binary mask to each one of the plurality of N frames of the ultrasound video.

26. A method for masking an ultrasound image, the method executed in a computing environment comprising one or more processors and memory, the method comprising:

automatically computing within the ultrasound image a set of keypoints that define an estimated shape of an ultrasound beam image within the ultrasound image;

automatically selecting, using the set of keypoints, a beam geometry from amongst a set of known beam geometries;

automatically modifying the set of keypoints based on the beam geometry to generate a modified set of keypoints that defines a modified shape of the ultrasound beam image;

automatically computing a binary mask configured to mask pixels around the modified shape of the ultrasound beam image, using at least the modified set of keypoints and the beam geometry; and automatically computing and outputting a masked ultrasound image using at least the binary mask.

27. A non-transitory computer readable medium storing computer executable instructions which, when executed by at least one computer processor, cause the at least one computer processor to carry out the method of claim 26.

28. A method for masking an ultrasound video, the method executed in a computing environment comprising one or more processors and memory, the method comprising:

automatically computing within the ultrasound video a set of keypoints that define an estimated shape of an ultrasound beam image within the ultrasound video;

automatically selecting, using the set of keypoints, a beam geometry from amongst a set of known beam geometries;

repeating a process for each one of a plurality of N frames of the ultrasound video, the process comprising automatically modifying the set of keypoints based on the beam geometry to generate a modified set of keypoints that defines a modified shape of the ultrasound beam image;

computing an averaged set of keypoints from an N number of modified sets of keypoints;

automatically computing a binary mask configured to mask pixels around the modified shape of the ultrasound beam image, using at least the averaged set of keypoints and the beam geometry; and automatically computing and outputting a masked ultrasound video by applying the binary mask to each one of the plurality of N frames of the ultrasound video.

29. A non-transitory computer readable medium storing computer executable instructions which, when executed by at least one computer processor, cause the at least one computer processor to carry out the method of claim 28.

* * * * *